United States Patent
Rapaport

(10) Patent No.: US 9,457,056 B2
(45) Date of Patent: Oct. 4, 2016

(54) PEPTIDES COMPRISING ALTERNATING HYDROPHOBIC AND ANIONIC AMINO ACIDS FOR TREATMENT OF OSTEOPOROSIS

(75) Inventor: Hanna Rapaport, Lehavim (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 785 days.

(21) Appl. No.: 12/746,168

(22) PCT Filed: Dec. 3, 2008

(86) PCT No.: PCT/IL2008/001570
§ 371 (c)(1),
(2), (4) Date: Aug. 11, 2010

(87) PCT Pub. No.: WO2009/072119
PCT Pub. Date: Jun. 11, 2009

(65) Prior Publication Data
US 2010/0297096 A1    Nov. 25, 2010

Related U.S. Application Data

(60) Provisional application No. 60/992,109, filed on Dec. 4, 2007.

(51) Int. Cl.
| A61K 38/04 | (2006.01) |
| A61K 38/16 | (2006.01) |
| A61K 38/18 | (2006.01) |
| A61K 38/03 | (2006.01) |
| C07K 7/04  | (2006.01) |

(52) U.S. Cl.
CPC ............. *A61K 38/03* (2013.01); *A61K 38/16* (2013.01); *A61K 38/18* (2013.01); *A61K 38/1875* (2013.01); *C07K 7/04* (2013.01)

(58) Field of Classification Search
None
See application file for complete search history.

(56) References Cited

U.S. PATENT DOCUMENTS

| 4,792,525 A | 12/1988 | Ruoslahti et al. | |
| 4,988,621 A | 1/1991 | Ruoslahti et al. | 435/240.2 |
| 5,280,040 A | 1/1994 | Labroo et al. | 514/422 |
| 5,670,483 A | 9/1997 | Zhang et al. | 514/14 |
| 5,695,997 A | 12/1997 | Ruoslahti et al. | 435/375 |
| 5,955,343 A | 9/1999 | Holmes et al. | 435/240.1 |
| 6,241,734 B1 | 6/2001 | Scribner et al. | 606/93 |
| 6,258,778 B1 | 7/2001 | Rodgers et al. | |
| 6,291,428 B1 | 9/2001 | Macaulay et al. | 514/12 |
| 6,492,525 B1 | 12/2002 | Bertrand et al. | 548/101 |
| 6,548,630 B1 | 4/2003 | Zhang et al. | 530/300 |
| 6,613,054 B2 | 9/2003 | Scribner et al. | 606/93 |
| 6,800,481 B1 | 10/2004 | Holmes et al. | 435/401 |
| 6,977,077 B1 | 12/2005 | Hock et al. | 424/198.1 |
| 7,008,433 B2 | 3/2006 | Voellmicke et al. | 606/93 |
| 7,153,307 B2 | 12/2006 | Scribner et al. | 606/93 |
| 7,163,920 B2 | 1/2007 | Dhanaraj et al. | 514/16 |
| 2004/0018961 A1 | 1/2004 | Stupp et al. | |
| 2004/0120922 A1 | 6/2004 | Burke | 424/78.27 |
| 2005/0181973 A1 | 8/2005 | Genove et al. | 514/2 |
| 2005/0208589 A1* | 9/2005 | Stupp et al. | 435/7.1 |
| 2006/0025524 A1 | 2/2006 | Schneider et al. | 530/326 |
| 2006/0084607 A1* | 4/2006 | Spirio | A61K 9/0019 514/21.4 |
| 2006/0154852 A1* | 7/2006 | Boden et al. | 514/2 |
| 2007/0233249 A1 | 10/2007 | Shadduck | 623/17.11 |

FOREIGN PATENT DOCUMENTS

| JP | 06192290 | 7/1994 |
| JP | 2007105186 | 4/2007 |
| WO | WO 2005/003292 A2 | 1/2005 |
| WO | WO 2006/014570 A2 | 2/2006 |
| WO | WO 2007/148334 A1 | 12/2007 |

OTHER PUBLICATIONS

Technical Information from Thermo Electron Corp. 2004; 2 pgs.*
Addadi, L. and Weiner, S. (1985) Interactions between acidic proteins and crystals: stereochemical requirements in biomineralization. *Proc Natl Acad Sci USA* 82(12):4110-4114.
Blouin, S. et al., (2006) Evaluation of an injectable bone substitute (βTCP/hydroxyapatite/hydroxy-propyl-methyl-cellulose) in severely osteopenic and aged rats. *Journal of Biomedical Materials Research part A* 78A(3):570-80.
Bolander, Mark E. (1992) Regulation of fracture repair by growth factors. *Proc Soc Exp Biol Med* 200(2):165-170.
Bonnik, Sydney L. (2006) Osteoporosis in men and women. *Clin Cornerstone* 8(1):28-39.
Boskey, Adele L. (1998) Biomineralization: conflicts, challenges, and opportunities. *J Cell Biochem Suppl* 30-31:83-91.
Caplan, M. R. et al., (2000) Self-assembly of a beta-sheet protein governed by relief of electrostatic repulsion relative to van der Weals attraction. *Biomacromolecules* 1(4):627-631.
Collier, Joel H. and Messersmith, Phillip B. (2003) Enzymatic modification of self-assembled peptide structures with tissue transglutaminase. *Bioconjugate Chem* 14(4):748-755.
Colombier, M. L. et al., (1999) A Single Low Dose of RGTA®, a New Healing Agent, Hastens Wound Maturation and Enhances Bone Deposition in Rat Craniotomy Defects. *Cells Tissues Organs* 164(3):131-140.
Danilevicius, C. F. et al., (2007) Bone metabolism and vascular calcification. *Braz J Med Biol Res* 40(4):435-442.
DeGrado, W. F. and Lear, J. D. (1985) Induction of peptide conformation at apolar water interfaces. 1. A study with model peptides of defined hydrophobic periodicity. *J Am Chem Soc* 107(25):7684-7689.

(Continued)

Primary Examiner — Kevin S Orwig
(74) Attorney, Agent, or Firm — Winston & Strawn LLP

(57) ABSTRACT

The present invention provides methods for prevention, prevention of progression, and treatment of osteoporosis and pre-osteoporotic conditions comprising direct administering to osteoporetic bone of a composition comprising amphiphilic peptides and peptide matrices thereof, useful in promoting biomineralization, local osteoporetic medications and inducing bone repair.

22 Claims, 5 Drawing Sheets

(56) References Cited

OTHER PUBLICATIONS

Delange, G. L. and Donath, K. (1989) Interface between bone tissue and implants of solid hydroxyapatite or hydroxyapatite-coated titanium implants. *Biomaterials* 10(2):121-125.
Erbe, Erik M. et al., (2001) Comparison of a new bisphenol-a-glycidyl dimethacrylate-based cortical bone void filler with polymethyl methacrylate. *Eur Spine J* 10(Suppl 2):S147-S152.
Ganss, B. et al., (1999) Bone sialoprotein. *Crit Rev Oral Biol Med* 10(1):79-98.
Gilbert, Michele et al., (2000) Chimeric peptides of statherin and osteopontin that bind hydroxyapatite and mediate cell adhesion. *J Biol Chem* 275(21):16213-16218.
Goldberg, H. A. et al., (2001) Binding of bone sialoprotein, osteopontin and synthetic polypeptides to hydroxyapatite. *Connect Tissue Res* 42(1):25-37.
He, Gen et al., (2005) Spatially and temporally controlled biomineralization is facilitated by interaction between self-assembled dentin matrix protein 1 and calcium phosphate nuclei in solution. *Biochemistry* 44(49):16140-16148.
Hollinger, Jeffrey O. and Kleinschmidt, James C. (1990) The Critical Size Defect as an Experimental Model to Test Bone Repair Materials. *J Craniofacial Surg* 1(1):60-68.
Hollinger, Jeffrey O. et al., (2008) Accelerated fracture healing in the geriatric, osteoporotic rat with recombinant human platelet-derived growth factor-bb and an injectable beta-tricalcium phosphate/collagen matrix. *J Orthop Res* 26(1):83-90.
Holmes, Todd C. et al., (2000) Extensive neurite outgrowth and active synapse formation on self-assembling peptide scaffolds. *Proc Natl Acad Sci USA* 97(12):6728-6733.
Hunter, Graeme K. et al., (1996) Nucleation and inhibition of hydroxyapatite formation by mineralized tissue proteins. *Biochem J* 317(1):59-64.
Hunziker, E.B.(2001) Articular cartilage repair: basic science and clinical progress. A review of the current status and prospects. *Osteoart Cart* 10(6):432-463.
Iijima, Mayumi et al., (1998) Effects of Ca addition on the formation of octacalcium phosphate and apatite in solution at pH 7.4 and at 37° C. *Journal of Crystal Growth* 193(1-2):182-188.
Ilvesaro, Joanna M. et al., (1998) Inhibition of bone resorption in vitro by a peptide containing the cadherin cell adhesion recognition sequence HAV is due to prevention of sealing zone formation. *Exp cell Res* 242(1):75-83.
Isenberg, Hila et al., (2006) Elasticity of crystalline beta-sheet monolayers. *J Am Chem Soc* 128(38):12468-12472.
Jayawarna, Vineetha et al., (2006) Nanostructured Hydrogels for Three-Dimensional Cell Culture Through Self-Assembly of Fluorenylmethoxycarbonyl—Dipeptides. *Adv Mater* 18(5):611-614.
Koh, Chester J. and Atala, Anthony (2004) Tissue Engineering, Stem Cells, and Cloning: Opportunities for Regenerative Medicine. *J Am Soc Nephrol* 15(5):1113-1125.
Kokubo, T. et al., (1990) Solutions able to reproduce in vivo surface-structure changes in bioactive glass-ceramic A-W$^3$. *J Biomed Mater Res* 24(6):721-34.
LeGeros, Racquel Zapanta (2002) Properties of osteoconductive biomaterials: calcium phosphates. *Clin Orthop Relat Res* 395:81-98.
Mann, Stephen (1988) Molecular recognition in biomineralization. *Nature* 332(6160):119-124.
Matsuyama, Yukihiro et al., (2004) Vertebral reconstruction with biodegradable calcium phosphate cement in the treatment of osteoporotic vertebral compression fracture using instrumentation. *J Spinal Disord Tech* 17(4):291-296.
Middleton, E. T. et al., (2008) The safety and efficacy of vertebroplasty using Cortoss cement in a newly established vertebroplasty service. *Br J Neurosurg* 22(2):252-256.
Oldberg, Ake et al., (1988) The primary structure of a cell binding bone sialoprotein. *J Biol Chem* 263(36):19430-19432.
Oliveira, A. L. et al., (2003) Nature-inspired calcium phosphate coatings: present status and novel advances in the science of mimicry. *Current Opinion in Solid State & Materials Science* 7(4-5):309-318.
Ou-Yang, H. et al., (2000) Two-Dimensional Vibrational Correlation Spectroscopy of In Vitro Hydroxyapatite Maturation. *Biopolymers (Biospectroscopy)* 57:129-139.
Ozbas, Bulent et al., (2004) Characterization of semiflexible fibril networks formed via intramolecular folding and self assembly of amphiphilic B-hairpin molecules. Abstracts of Papers American Chemical Society 228(2):U374-U375.
Phillips, Frank M. et al., (2006) In vivo BMP-7 (OP-1) enhancement of osteoporotic vertebral bodies in an ovine model. *Spine J* 6(5):500-506.
Ramachandran, Sivakumar et al., (2005) Repeated rapid shear-responsiveness of peptide hydrogels with tunable shear modulus. *Biomacromolecules* 6(3):1316-1321.
Rapaport, Hana et al., (2000) Two dimentional order in beta-sheet peptide monolayer. *J Am Chem Soc* 122(50):12523-12529.
Rapaport, Hanna et al., (2002) Assembly of triple-stranded β-sheet peptides at interfaces. *J Am Chem Soc* 124(32):9342-9343.
Segman-Magidovich, Shlomit et al., (2008) Matrices of Acidic b-Sheet Peptides as Templates for Calcium Phosphate Mineralization. *Adv Mater* 20(11):2156-2161.
Silva, Gabriel A. et al., (2004) Selective differentiation of neural progenitor cells by high-epitope density nanofibers. *Science* 303(5662):1352-1355.
Stromsoe, Knut (2004) Fracture fixation problems in osteoporosis. *Injury* 35(2):107-113.
Traub, Wolfie et al., (1989) Three-dimensional ordered distribution of crystals in turkey tendon collagen fibers. *Proc Natl Acad Sci USA* 86(24):9822-9826.
Valentin, Andreas H. and Weber, J. (2004) Receptor technology-cell binding to P-15: a new method of regenerating bone quickly and safely—preliminary histomorphometrical and mechanical results in sinus floor augmentations. *Keio J Med* 53(3):166-171.
Wang et al., (2008) Altered bioreactivity and limited osteoconductivity of calcium sulfate-based bone cements in the osteoporotic rat spine. The Spine Journal 8:340-50.
Weiner, Stephen and Addadi, Lia (1997) Design strategies in mineralized biological materials. *J Mater Chem* 7(5):689-702.
Young, Marian F. et al., (1992) Structure, expression and regulation of the major noncollagenous matrix proteins of bone. *Clin Orthop Relat Res* 281:275-294.
Zhang, Shuguang et al., (1993) spontaneous assembly of a self-complemetary oligopeptide to form a stable macroscopic membrane. *Proc Natl Acad Sci USA* 90(8):3334-3338.
Zhang, S. (2003) Fabrication of novel biomaterials through molecular self-assembly. *Nat Biotechnol* 21(10):1171-1178.
International Search Report, PCT/IL2008/001570 Jun. 3, 2009.
International Search Report, PCT/IL2007/000743 Nov. 6, 2007.
Database WPI week 200736 Thomson Scientific, London, GB; AN 2007-382871 XP002528834.
Database Geneseq [online] Mar. 21, 1995 "peptide for treating diseases related to anti-DNA antibodies" XP002455844 retrieved from EBI accession No. GSP:AAR57394 Database accession No. AAR57394 abstract.
Database Geneseq [online] Mar. 21, 1995 "peptide for treating diseases related to anti-DNA antibodies" XP002455845 retrieved from EBI accession No. GSP:AAR57393 Database accession No. AAR57393 abstract.
Geneseq database accession No. AAM95164 WO 2001/55320.
U.S. Appl. No. 12/305,588 Requirement for Restriction/Election Mar. 29, 2012.
Rapaport et al., (2008) Hydrogel Scaffolds of Amphiphilic and Acidic β-Sheet Peptides. Advanced Functional Materials 18(19): 2889-2896.
Saito et al., (2002) Osteogenic response of hydroxyapatite cement implanted into the femur of rats with experimentally induced osteoporosis. Biomaterials 23(13): 2711-2716.
Stendahl et al., (2006) Intermolecular forces in the self-assembly of peptide amphiphile nanofibers. Advanced Functional Materials 16(4): 499-508.

\* cited by examiner

Figure 1A
Figure 1B
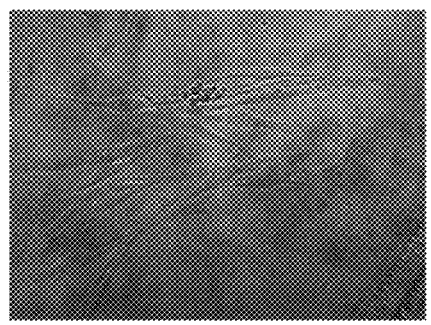
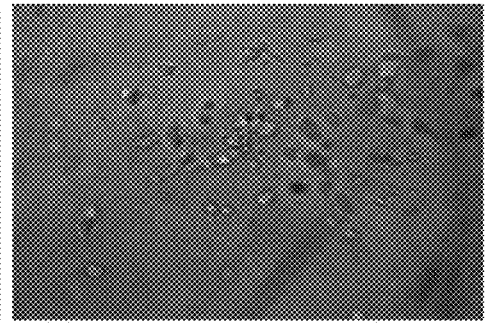

PEPTIDES COMPRISING ALTERNATING HYDROPHOBIC AND ANIONIC AMINO ACIDS FOR TREATMENT OF OSTEOPOROSIS

This application is a 371 filing of International Patent Application PCT/IL2008/001570 filed Dec. 3, 2008, which claims the benefit of application No.60/992,109 filed Dec. 4, 2007.

FIELD OF THE INVENTION

The present invention relates to therapeutic methods for treatment and prevention of progression of osteoporosis and related conditions by direct, local or intralesional administration, to the bone, of compositions comprising amphiphilic peptides and hydrogel matrices formed by these peptides.

BACKGROUND OF THE INVENTION

Osteoporosis

Osteoporosis is defined as a disease characterized by low bone mass and microarchitecture deterioration of bone tissue, leading to enhanced bone fragility and a consequent increase in fracture risk. The most frequent osteoporotic fractures are those of the proximal femur, distal forearm, and vertebrae. Osteoporotic vertebral fractures are associated with a significant increase in morbidity and mortality including severe and chronic back pain, functional limitation, height loss, spinal deformity, and disability.

A common occurrence in older people is compression fractures of the vertebrae that is commonly treated by vertebroplasty procedure in which cement is injected into a fractures vertebra. In his clinical procedure bone cement is injected at high pressure into the interior of a vertebral body, without the prior formation of a cavity. Vertebroplasty is an invasive procedure and has also been applied to vertebral haemangiomas and painful lesions caused by metastatic disease. An injection of the liquid cement with a cannula is made into the vertebral body. The injectate is typically a polymethyl methacrylate cement (PMMA) used more commonly to fix joint prostheses to bone. The method produces an in situ polymerization and gives immediate results on bone pain. PMMA has some disadvantages including excess heat generated during the polymerization process, and the possibility of inducing giant cell granulomas and fibrous reactions. Adjacent vertebral overload has been reported with maximal PMMA filling, possibly provoking fractures. Systems, devices and methods for placing material directly into bones are described for example in U.S. Pat. Nos. 7,153,307, 7,008,433, 6,241,734, 6,613,054 and in US publication number US 2007/0233249.

Another common treatment applicable to vertebra fractures is kyphoplasty in which a balloon is first inflated inside the vertebra that is next filled with a fixing material or an implant. This treatment reduces the risk of cement migration, yet it suffers other limitations as poor contact between the filler and the bone tissue.

Composite cements containing methacrylic polymers and HA have been proposed but all these biomaterials are not resorbable or biodegradable. Tri Calcium phosphate bone substitutes are biocompatible, bioactive, and biodegradable with osteoconductive properties.

The association of HA and beta-tri calcium phosphate (beta-TCP), in suitable proportions provides biphasic calcium phosphate (BCP) ceramics whose bioactivity depends on the HA/beta-TCP ratio. Treatment of vertebroplasty using calcium phosphate cement (CPC) alone in such patients has been reported, but complications such as recrushing of the vertebra and prolapse of the cement into the spinal canal may occur. Matsuyama et al. (2004) have showed that vertebral reconstruction with biodegradable CPC in the treatment of osteoporotic vertebral compression fracture using instrumentation (such as screws to fix adjacent vertebrae) was a safe and useful surgical treatment. Fracture fixation in osteoporosis is a critical factor since the surrounding bone is weak to begin with (Kraut 2004). The use of BCP granules in the injectable form has been evaluated in osteoporotic rats to test their potent restorative properties on bone mass and bone microarchitecture (Blouin et al. 2006). It was concluded that biomaterial trials must be conducted with long-term implantation periods, in aged osteoporotic animals.

Hollinger et al. (2007) have studied whether recombinant human platelet-derived growth factor-BB (rhPDGF-BB) delivered in an injectable beta-tricalcium phosphate/collagen matrix would enhance tibial fracture healing in geriatric osteoporotic rats.

Ilvesaro et al. (1998) described inhibition of bone resorption in vitro by a peptide containing the cadherin cell adhesion recognition sequence HAV (His-Ala-Val), and suggested that the tight attachment of osteoclasts to the bone surface in the sealing zone area may be mediated by cadherin-like molecules.

Existing agents such as estrogen, bisphosphonates, fluoride, or calcitonin can prevent bone loss and induce a 3-5% increase of bone mass by refilling the remodeling space, but net bone formation is not significantly stimulated. The retention of bone by inhibition of bone turnover may not be sufficient protection against fracture risk for patients who already have significant bone loss. It is suggested that anabolic agents that increase bone strength by stimulating bone formation preferentially may provide better protection against fracture in patients with established osteoporosis.

Known metabolites and hormones affecting osteoporosis (review by Lopes and Pereira 2007) are for example, parathyroid hormone (PTH) and its 1-34 fragment (described for example in U.S. Pat. No. 6,977,077), administered preferably by subcutaneous injection, daily in >5 microgram/Kg/day; Matrix Gla proteins (MGP) which inhibit mesenchymal differentiation into osteogenic cell lines by blocking the action of BMP (bone morphogenic proteins) inducing osteopenia; Osteopontin (OPN) a matrix protein that binds to osteoclasts through specific integrin and functions as an important inhibitor of calcification; Osteoprotegrin (OPG), a soluble cytokine of the tumor necrosis factor (TNF) receptor family produced by many cells and its absence was shown to be involved in osteoporosis and calcification of the vascular wall of the aorta and renal arteries. Other agents, such as bisphosphonates operate by preventing the resorption of bone. U.S. Pat. No. 5,280,040 discloses compounds described as useful in the treatment of osteoporosis by preventing bone resorption.

Bisphosphonates, formerly called diphosphonates are compounds characterized by two C—P bonds. There are a number of known pharmacologically active bisphosphonates including alendronate, clodronate, etidronate, ibandronate, icadronate, pamidronate, risedronate, tiludronate and zoledronate. The main effect of these pharmacologically active bisphosphonates is to inhibit resorption both in vitro and in vivo. These effects are related to the marked affinity of these compounds for solid-phase calcium phosphate, on the surface of bone. There is a general consensus that the bisphosphonates act by inhibiting the activity of osteoclasts.

Osteoclasts are inhibited when they come into contact with bisphosphonates-containing bone. This supports the hypothesis that bisphosphonates are deposited onto bone because of their strong affinity for the mineral, and that the osteoclasts are then inhibited when they start to engulf bisphosphonates-containing bone.

The bisphosphonates investigated up to now appear to be absorbed, stored, and excreted unaltered in the body. Thus, bisphosphonates seem to be non-biodegradable, both in animals and in solution. The intestinal absorption lies between 1% and 10%. Between 20% and 50% of the absorbed bisphosphonate is localized to the bone, the remainder being rapidly excreted in the urine. The half-life of circulating bisphosphonates is short, in the rat only of the order of minutes and in human about 2 hours. Although the nitrogen-containing bisphosphonates such as alendronate and pamidronate, have been shown to be effective in preventing the bone loss, these drugs also appear capable of causing injury to the upper gastrointestinal tract in addition ulcerations and, especially, osteonecrosis of the jaws and their have been several case reports of severe oesophagitis in patients treated with alendronate. Alendronate has also been shown to cause erosions and ulcers in the human stomach and to interfere with the healing of pre-existing lesions when given to healthy volunteers at doses that are prescribed for the treatment of osteoporosis and Pagets disease of bone.

Tissue engineering includes the provision of cells or of a natural or synthetic scaffold that serves as an architectural support onto which cells may attach, proliferate, and synthesize new tissue to replace tissue losses due to disease, trauma or age. The trend in tissue engineering in general is to utilize biomaterials to promote healing or tissue regeneration. In orthopedics and dentistry the clinical focus transforms from traditional metal and other inorganic implants, plates, screws and cements to biologically based products for mineralized tissue regeneration. Natural polymers are of major interest in tissue engineering since they tend to be biocompatible and biodegradable and may have the potential to enhance cell adhesion and proliferation. Additionally, such material substrates can be prepared in various forms and shapes, including strips, sheets, sponges and beads for implantation.

Bone is a unique type of tissue that comprises both organic and inorganic phases, that undergoes modeling and remodeling wherein old bone is lost (resorption) and new bone is formed (formation/replacement). Bone formation may be enhanced either by recruiting osteoblasts, the bone forming cells, or by inhibiting recruitment or activity of osteoclasts, the bone resorbing cells. Osteoblasts and osteoclasts work together in a coordinated fashion to form and remodel bone tissue. The activities of these cells are regulated by a large number of cytokines and growth factors, many of which have now been identified and cloned.

There is a plethora of conditions which are characterized by the need to enhance bone formation or to inhibit bone resorption. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease, osteopenia, spinal fusion and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis.

Many materials have been utilized for bone repair. Synthetic materials are being developed in order to replace autologous harvesting problems and the health risks attendant with allogeneic material. Inorganic materials such as calcium phosphate and hydroxyapatite have been utilized as bone and dental fillers (reviewed in LeGeros, 2002) but lacking many of the extra cellular like functionalities, none can be considered entirely satisfactory in meeting the criteria required for successful tissue engineering.

Biomineralization of Bone

Biomineralization refers to the deposition of inorganic solids in biological systems. The natural mineralization of bone is considered to occur by deposition of hydroxyapatite (HA, having the chemical formula $Ca_{10}(PO_4)_6(OH)_2$), or its precursor forms in an organic extracellular matrix composed of collagen and other proteins, many of which are rich in acidic residues (Hunter, 1996; Teraub, 1989). The major role of collagen is to render the bone improved mechanical properties through an hierarchical composition of the organic fibers and aligned HA minerals (Lowenstam et al., 1989, Mann, S., 2001). Non-collagenous proteins (i.e. bone sialoprotein, osteopontin, osteocalcin, osteonectin and others, Young et al, 1992), isolated from bone extracellular matrices that are rich in acidic amino acids, have been proposed to be involved in the nucleation, and growth of carbonated apatite. Among these, sialoprotein, a glycosylated and sulphated phosphoprotein, found almost exclusively in mineralized connective tissues, is the most widely accepted protein linked to apatite nucleation (Ganss et al., 1999). Sialoprotein exhibits regions rich in both glutamic- and aspartic-acid residues (Oldberg et al, 1988) as well as the cell binding arginine-glycine-aspartate (RGD) motifs. Despite numerous studies aiming at unraveling the principles of apatite biomineralzation, detailed mechanisms that account for the role of acid rich proteins in this process, are yet to be elucidated.

Among the main properties of organic interfaces that may be contributing to nucleation of biominerals are electrostatic accumulation and structural correspondence. Electrostatic accumulation is considered to be the initial step in biomineralization. It is believed that one of the most essential properties of bone acid-rich proteins and possibly also collagen is their ability to control nucleation by charged amino acid residues on their surfaces. The primary residues are acidic and phosphorylated amino acids, which at biological pH, may expose charged functional groups, i.e. negatively charged carboxylate groups of glutamic acid and aspartic acid as well as negatively charged phosphates. (Addadi, 1985; Mann, 1988).

Peptide Matrices

Recent developments in the study of peptide self-assembly matrices have advanced the understanding of the relationship between amino acid composition, molecular assembly forms and interaction of these materials with cells. Certain peptides and proteins have been shown to promote osteogenic cell adhesion. A 15-mer peptide fragment of collagen 1 α1has been designed to include cell binding domain for mesenchymal progenitor cells. This fragment is commercially available as Pepgen P-15® in combination with anorganic bovine derived bone mineral as particles or cement for bone grafting in patients with periodontal osseous defects (Valentin and Weber, 2004). Gilbert, et al. (2000) teach a fusion peptide of two extracellular matrix proteins, statherin and osteopontin that binds HA and mediates cell adhesion. The chimeric peptide was shown to have utility in tissue engineering and vaccine applications. Goldberg, et al. (2001) teach synthetic poly-L-glutamic acid and poly-L-aspartic acid peptides and their ability to bind HA. He, et al. (2003) report that the acidic protein dentin matrix protein 1 (DMP 1) assembles into acidic clusters that are claimed to nucleate the formation of HA in vitro.

International patent application WO 2005/003292 relates to a composition useful for making homogenously mineralized self-assembled peptide amphiphile nanofibers and nanofiber gels which may be prepared with appropriate phosphate and calcium solutions to yield mineral templated matrices.

U.S. Pat. Nos. 5,670,483; 5,955,343; 6,548,630 and 6,800,481 relate to amphiphilic peptides having alternating hydrophobic and hydrophilic residues, and their resultant macroscopic membranes. Specifically, two peptides having the amino acid sequences (AEAEAKAK)$_2$ and (ARARADAD)$_2$ were shown to self assemble into macroscopic membranes useful for in vitro culturing of cells and biomaterial applications. The former sequence was originally found in a region of alternating hydrophobic and hydrophilic residues in a yeast protein called zuotin.

US Patent Publication No. US 2005/0181973 discloses a self-assembling peptide comprising two domains, the first comprising complementary alternating hydrophobic and hydrophilic amino acids that are overall neutrally charged with equal number of positively and negatively charged amino acids, and self-assemble into a macroscopic structure, including hydroegls, when present in unmodified form; and a second domain comprises a biologically active peptide motif or a target site for an interaction with a biomolecule. That application further teaches that replacement of the positively charged residues, lysine (K) and arginine (R), by negatively charged residues, such as aspartate (D) and glutamate (E), prevents peptide self-assembly into macroscopic structures and only β-sheet and not macroscopic structures are formed in the presence of salt. The VE20 peptide, a 20-mer peptide comprising alternating valine (V) and glutamate (E) amino acids, was disclosed as not able to self-assemble to form macroscopic structures.

US Patent Publication No. US 2006/0025524 discloses a method for making a hydrogel from a solution of peptides, mainly peptides containing Val-Lys repeats or peptides with at least one positively-charged residue per 6 amino acids, which undergo change in conformation from random coil to β-hairpin secondary structures, that promote hydrogel formation. The hydrogel is formed by alteration peptide concentration or one or more environmental signals or stimuli (e.g., change in pH, ionic strength, specific ion concentration, and/or temperature of the solution).

US Patent Publication No. 2004/0120922 discloses a method for promoting bone formation by administering of amine polymers.

The "RGD" (Arg-Gly-Asp) tri-peptide sequence, which occurs in fibronectin and has been shown to promote cell adhesion and growth, has been disclosed in inter alia, U.S. Pat. Nos. 4,988,621; 4,792,525 and 5,695,997. U.S. Pat. No. 6,291,428 teaches peptides comprising the RGD amino acid sequence for promoting in situ bone mineralization.

The inventor of the present invention reported amphiphilic peptides that form β-strand monolayers when spread at air-water interfaces (Rapaport, 2000; Rapaport, 2002, WO 2007/148334). Peptides of seven to 17 amino acid residues were found to form crystalline arrays with coherence lengths of about 100 to about 1000 Å. A 30-residue peptide, which incorporates proline residues to induce reverse turns, was designed to form an ordered triple stranded β-sheet monolayer at the air water interface.

Specific methods for prevention and treatment of osteoporosis and pre-osteoporotic conditions by local administration of compositions comprising these peptides were neither taught nor suggested in those publications.

There is an unmet medical need for improved compositions and methods for prevention of progression and treatment of osteoporosis and pre-osteoporotic conditions.

SUMMARY OF THE INVENTION

The present invention provides therapeutic uses of amphiphilic peptides and pharmaceutical compositions comprising them for treatment and prevention of progression of osteoporosis and pre-osteoporotic conditions by direct administration into deficient, deteriorated or injured bone and in particular into low bone mineral density sites. The amphiphilic peptides comprise predominantly acidic amino acids, which are capable, alone or in combination with ions and minerals, of forming β-sheet assemblies and hydrogels at physiological pH and serve as scaffolds for mineralization directly at the bone site.

It is now disclosed in accordance with the present invention that certain compositions comprising amphiphilic peptides can be efficiently and safely used for treatment and prevention of progression of bone defects associated with osteoporetic conditions, when administered directly to the bone. The peptides comprise alternating hydrophobic and hydrophilic residues, wherein the hydrophilic residues are predominantly acidic, self-assemble into three dimensional structures within aqueous solution, form fibrous matrices with n-sheet fibers, and act as scaffolds for mineralization. Furthermore, the therapeutic methods disclosed optionally comprise peptide hydrogels or matrices which are carriers or depot for bioactive agents including active proteins, growth factors, hormones, antibiotics and in particular bone antiresorptive agents such as bisphosphonates.

The present invention is based in part on the finding that amphiphilic and acidic β-sheet peptide matrices are useful, due to their structure and functionality, for direct, local or intralesional treatment of osteoporotic bones and pre-osteoporotic conditions that are at high fracture risk. It is now disclosed, for the first time, that compositions comprising such peptides are suitable and preferable for local administration into osteoporotic or pre-osteoporotic bone, and are biocompatible, safe, non-immunogenic and biodegradable and therefore superior for administering in methods for prevention, prevention of progression, and treatment of osteoporosis. Compositions comprising amphiphilic peptides administered according to the present invention serve as a template or nucleation center for in vitro and in situ biomineralization, to mimic the formation of natural bone tissue thereby providing rapid bone regeneration, increasing bone mineral density and reducing risk for fractures.

According to one aspect the invention provides a method for the treatment, prevention or prevention of progression of osteoporosis and pre-osteoporotic condition said method comprising administering to a subject in need of such treatment a therapeutically effective amount of a pharmaceutical composition comprising at least one amphiphilic peptide comprising at least 2 dyads of alternating hydrophobic/hydrophilic amino acid residues, or a derivative or a salt thereof, capable of forming a β-sheet structure and promoting biomineralization, wherein the peptide comprises:

i. 2-20 pairs of hydrophobic-hydrophilic alternating amino acid residues wherein the hydrophilic amino acid residue is selected from the group consisting of: a negatively charged amino acid, a hydroxyl-containing amino acid, and a phosphorylated-hydroxyl-containing amino acid; and ii. no more than 10% positively charged amino acid residues.

According to a specific embodiment the pharmaceutical composition further comprises an aqueous medium in which the peptide is dissolved. Preferably, the pharmaceutical composition forms a hydrogel at physiological conditions.

According to some embodiments the at least one amphiphilic peptide is 4-40 amino acids in length. According to some embodiments the at least one amphiphilic peptide is 7-28 amino acids in length. According to some embodiments the peptide further comprises at least one terminal Proline (Pro) residue. According to certain embodiments the peptide further comprises two terminal Pro residues. According to one embodiment the hydrophobic amino acid is selected from the group consisting of Phenylalanine (Phe), Leucine (Leu), Isoleucine (Ile), Valine (Val) and Alanine (Ala). According to certain embodiments the hydrophobic amino acid is Phe or Leu. According to some embodiments the hydrophilic amino acid is selected from the group consisting of: Glutamic acid (Glu), Aspartic acid (Asp), Tyrosine (Tyr), Serine (Ser), Threonine (Thr), Phosphoserine (Ser($PO_4$)), Phosphotyrosine (Thr($PO_4$)), and Phosphotyrosine (Tyr ($PO_4$)).

According to another embodiment, the peptide comprises an amino acid sequence according to Formula I:

X-(hydrophobic-hydrophilic)$_n$-B                    (Formula I)

wherein n designates an integer of 2-20, hydrophobic designates a hydrophobic amino acid residue, hydrophilic designates a hydrophilic amino acid residue, X designates Pro, Pro-hydrophilic or represents the peptide's amino terminus, and B is Pro or represents the peptide's carboxy terminus.

According to some embodiments the amino terminus is modified, e.g., it may be acetylated. According to some embodiments the carboxy terminus is modified, e.g., it may be amidated.

According to a specific embodiment, the peptide comprises an amino acid sequence selected from the group consisting of:
X-(Phe-Glu)$_n$-B
X-(Phe-Asp)$_n$-B
X-(Leu-Glu)$_n$-B
X-(Leu-Asp)$_n$-B
wherein n designates an integer of 2-20, X designates Pro, Pro-hydrophilic or represents the peptide's amino terminus, hydrophilic designates a hydrophilic amino acid residue, and B is Pro or represents the peptide's carboxy terminus.

According to some embodiments the amino terminus is modified, e.g., it may be acetylated. According to some embodiments the carboxy terminus is modified, e.g., it may be amidated.

According to one embodiment the composition comprises an amphiphilic peptide comprising a sequence selected from the group consisting of:
Pro-Glu-(Phe-Glu)$_9$ (SEQ ID NO: 36) wherein 0 to 6 of the 9 (Phe-Glu) repeats can be absent;
Glu-(Phe-Glu)$_9$-Pro (SEQ ID NO: 37) wherein 0 to 6 of the 9 (Phe-Glu) repeats can be absent;
Pro-(Ser-Phe)$_9$-Ser-Pro SEQ ID NO: 38) wherein 0 to 6 of the 9 (Ser-Phe) repeats can be absent;

Pro-(SerPO$_4$-Phe)$_9$-SerPO$_4$-Pro (SEQ ID: 39) wherein 0 to 6 of the 9 (SerPO$_4$-Phe) repeats can be absent;
Pro-(TyrPO$_4$-Phe)$_9$-TyrPO$_4$-Pro (SEQ ID NO: 40) wherein 0 to 6 of the 9 (TyrPO$_4$-Phe) repeats can be absent;
Pro-(Glu-Leu)$_9$-Glu-Pro (SEQ ID NO: 41) wherein 0 to 6 of the 9 (Glu-Leu) repeats can be absent;
Pro-(Asp-Phe)$_9$-Asp-Pro (SEQ ID NO: 42) wherein 0 to 6 of the 9 (Asp-Phe) repeats can be absent;
Pro-(Asp-Leu)$_9$-Asp-Pro (SEQ ID NO: 43) wherein 0 to 6 of the 9 (Asp-Phe) repeats can be absent;
Pro-(Ser-Leu)$_9$-Ser-Pro (SEQ ID NO: 44) wherein 0 to 6 of the 9 (SerPO$_4$-Leu) repeats can be absent;
Pro-(SerPO$_4$-Leu)$_9$-SerPO$_4$-Pro (SEQ ID NO: 45) wherein 0 to 6 of the 9 (SerPO$_4$-Leu) repeats can be absent;
Pro-(TyrPO$_4$-Leu)$_9$-TyrPO$_4$-Pro (SEQ ID NO: 46) wherein 0 to 6 of the 9 (TyrPO$_4$-Leu) repeats can be absent;
Pro-(Glu-Phe-Ser-Phe)$_9$-Glu-Pro (SEQ ID NO: 47) wherein 0 to 6 of the 9 (Glu-Phe-Ser-Phe) repeats can be absent;
Pro-(SerPO$_4$-Phe-Ser-Phe)$_4$-Ser-Pro (SEQ ID NO: 12) wherein 0 to 3 of the 4 (SerPO$_4$-Phe-Ser-Phe) repeats can be absent;
Pro-(SerPO$_4$-Phe-Glu-Phe)$_4$Glu-Pro (SEQ ID NO: 13) wherein 0 to 3 of the 4 (SerPO$_4$-Phe-Glu-Phe) repeats can be absent;
Pro-(SerPO$_4$-Phe-Asp-Phe)$_4$-Asp-Pro (SEQ ID NO: 14) wherein 0 to 3 of the 4 (SerPO$_4$-Phe-Asp-Phe) repeats can be absent;
Pro-Glu-(Phe-Glu)$_n$-(Gly)$_m$-Arg-Gly-Asp-Z wherein Z is Ser, Gly or represents the peptide's carboxy terminus, n is an integer of 2-15 and m is an integer of 0-10;
(Phe-Glu)$_n$-(Gly)$_n$-Arg-Gly-Asp-Z where Z is Ser, Gly or represents the peptide's carboxy terminus, n is an integer of 2-15 and m is an integer of 0-10; and
Pro-(Asp-Phe)$_n$-Asp-Pro-(Gly)$_n$-Arg-Gly-Asp-Z wherein Z is Ser, Gly or represents the peptide's carboxy terminus, n is an integer of 2-15 and m is an integer of 0-10.

According to a specific embodiment the composition comprises an amphiphilic peptide comprising a sequence selected from the group consisting of:

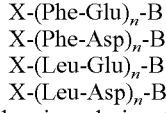

```
                                           (SEQ ID NO: 1)
Pro-Glu-Phe-Glu)₅;

(SEQ ID NO: 2)
Glu-Phe-Glu)₅-Pro;

(SEQ ID NO: 3)
Pro-(Ser-Phe)₅-Ser-Pro;

(SEQ ID NO: 4)
Pro-(SerPO₄-Phe)₅-SerPO₄-Pro;

(SEQ ID NO: 5)
Pro-(TyrPO₄-Phe)₅-TyrPO₄-Pro;

SEQ ID NO: 6)
Pro-(Glu-Leu)₅-Glu-Pro;

(SEQ ID NO: 7)
Pro-(Asp-Leu)₅-Asp-Pro;

(SEQ ID NO: 8)
Pro-(Ser-Leu)₅-Ser-Pro;

(SEQ ID NO: 9)
Pro-(SerPO₄-Leu)₅-SerPO₄-Pro;

(SEQ ID NO: 10)
Pro-(TyrPO₄-Leu)₅-TyrPO₄-Pro;
```

-continued

Pro-(Glu-Phe-Ser-Phe)$_4$-Glu-Pro;   (SEQ ID NO: 11)

Pro-(SerPO$_4$-Phe-Ser-Phe)$_4$-Ser-Pro;   (SEQ ID NO: 12)

Pro-(SerPO$_4$-Phe-Glu-Phe)$_4$-Glu-Pro;   (SEQ ID NO: 13)

Pro-(SerPO$_4$-Phe-Asp-Phe)$_4$-Asp-Pro;   (SEQ ID NO: 14)

Ala-Leu-Glu-(Phe-Glu)$_3$-Pro-Ala-(Glu-Phe)$_3$-Glu-Leu-Pro-Ala-Leu-Glu-(Phe-Glu)$_3$-Pro;   (SEQ ID NO: 15)

Pro-Glu-(Phe-Glu)$_2$-Lys-(Glu-Phe)$_2$-Glu-Pro;   (SEQ ID NO: 16)

Pro-Glu-(Phe-Glu)$_5$-(Gly)$_3$-Arg-Gly-Asp-Ser;   (SEQ ID NO: 17)

(Phe-Glu)$_3$-Pro-(Gly)$_3$-Arg-Gly-Asp-Ser;   (SEQ ID NO: 18)

Ac-Pro-Asp-(Phe-Asp)$_5$-Pro-NH$_2$;   (SEQ ID NO: 19);

Pro-Asp-(Phe-Asp)$_6$;   (SEQ ID NO: 20)

(Phe-Asp)$_6$;   (SEQ ID NO: 21)

Pro-Glu-(Phe-Glu)$_5$-Pro;   (SEQ ID NO: 22)

Pro-Asp-(Phe-Asp)$_5$-Pro-NH$_2$;   (SEQ ID NO: 23)

(Phe-Glu)$_5$;   (SEQ ID NO: 24)

(Phe-Glu)$_6$;   (SEQ ID NO: 25)

(Phe-Glu)$_7$;   (SEQ ID NO: 26)

Pro-Asp-(Phe-Asp)$_4$;   (SEQ ID NO: 27)

Pro-Asp-(Phe-Asp)$_6$;   (SEQ ID NO: 28)

Pro-Asp-(Phe-Asp)$_8$;   (SEQ ID NO: 29)

(Phe-Asp)$_5$;   (SEQ ID NO: 30)

(Phe-Asp)$_6$;   (SEQ ID NO: 31)

(Phe-Asp)$_7$;   (SEQ ID NO: 32)

Pro-Asp-(Phe-Asp)$_5$-Pro-Arg-Gly-Asp-Ser;   (SEQ ID NO: 33)

Pro-(Phe-Asp)$_3$-Pro;
and   (SEQ ID NO: 34)

Pro-(Phe-Asp)$_3$-Pro-(Gly)$_3$-Arg-Gly-Asp-Ser,   (SEQ ID NO: 35).

According to a specific embodiment, an amphiphilic peptide is provided comprising a sequence selected from the group consisting of:

Pro-Glu-(Phe-Glu)$_5$-Pro;   (SEQ ID NO: 22)

Pro-Asp-(Phe-Asp)$_5$-Pro-NH$_2$;   (SEQ ID NO: 23);

(Phe-Glu)$_5$;   (SEQ ID NO: 24)

(Phe-Glu)$_6$;   (SEQ ID NO: 25)

(Phe-Glu)$_7$;   (SEQ ID NO: 26)

Pro-Asp-(Phe-Asp)$_4$;   (SEQ ID NO: 27)

Pro-Asp-(Phe-Asp)$_6$;   (SEQ ID NO: 28)

Pro-Asp-(Phe-Asp)$_8$;   (SEQ ID NO: 29)

(Phe-Asp)$_5$;   (SEQ ID NO: 30)

(Phe-Asp)$_6$;   (SEQ ID NO: 31)

(Phe-Asp)$_7$;   (SEQ ID NO: 32)

Pro-Asp-(Phe-Asp)$_5$-Pro-Arg-Gly-Asp-Ser;   (SEQ ID NO: 33)

Pro-(Phe-Asp)$_3$-Pro;
and   (SEQ ID NO: 34)

Pro-(Phe-Asp)$_3$-Pro-(Gly)$_3$-Arg-Gly-Asp-Ser,   (SEQ ID NO: 35).

According to some embodiments the composition directly administered comprises at least two different peptide sequences, mixed or covalently linked. According to a specific embodiment the composition administered comprises a peptide analog, chemical derivative, or a pharmaceutically acceptable salt of the peptide. According to other embodiments the derivatives include phosphorylated, amidated and acetylated peptides. Additionally, the peptide sequences can be chemically bound to a hydrophobic moiety, i.e. a lipid tail, a repeat of hydrophobic amino acids, or to any molecule which may modulate the molecular self-assembly forms. One lysine residue per each about 9 amino acids or more can be incorporated along the peptide to increase solubility in aqueous solution and to improve synthesis and purification yields. In one embodiment the peptide comprises the sequence Pro-Glu-(Phe-Glu)$_2$-Lys-(Glu-Phe)$_2$-Glu-Pro where Lys is capable of inducing a reverse turn. According to some embodiments the peptides are provided as multimers comprising linked repeats of the same sequence or of different sequences. According to other embodiments, mixtures of peptides according to the invention are provided. Peptide mixtures and peptide multimers comprise peptides of similar lengths, or peptide of different length may also be mixed or linked together.

In another embodiment, another bioactive sequence is incorporated into the peptides administered according to the methods of the present invention. One non-limiting sequence is the trimer RGD (Arg-Gly-Asp), which is known to play a role in cell adhesion. According to some embodiments the peptide comprising the RGD sequence is selected from the group consisting of: Pro-Glu-(Phe-Glu)$_n$-(Gly)$_m$-

Arg-Gly-Asp, wherein n is an integer of 2-20 and m is an integer of 0-10; Pro-Glu-(Phe-Glu)$_n$-(Gly)$_m$-Arg-Gly-Asp-Z wherein Z is Ser, Gly or represents the peptide's carboxy terminus, n is an integer of 2-15 and m is an integer of 0-10; (Phe-Glu)$_n$-(Gly)$_m$-Arg-Gly-Asp-Z where Z is Ser, Gly or represents the peptide's carboxy terminus, n is an integer of 2-15 and m is an integer of 0-10; and Pro-(Asp-Phe)$_n$-Asp-Pro-(Gly)$_m$-Arg-Gly-Asp-Z wherein Z is Ser, Gly or represents the peptide's carboxy terminus, n is an integer of 2-15 and m is an integer of 0-10.

According to yet another embodiment, the compositions administered according to the methods of the present invention comprise peptides, proteins and other substances having osteogenic activity which are linked to or mixed with the amphiphilic peptides. Other active substances known to enhance bone and cartilage repair are angiotensinogen, angiotensin AI and its fragments and analogs, angiotensin AII and its fragments and analogs, bone morphogenic protein-2, bone morphogenic protein-4, bone morphogenic protein-6, bone morphogenic protein-7, transforming growth factor-beta, insulin-like growth factor, and parathyroid hormone (PTH).

According to another embodiment the composition administered according to the method of the present invention further comprises a pre-loaded mineral-salt solution or aggregates. According to a specific embodiment the composition comprises a calcium phosphate mineral selected from the group consisting of amorphous calcium phosphate, tricalcium phosphate and hydroxyapatite. According to yet another embodiment the composition comprises pre-loaded polysaccharides. According to a specific embodiment the polysaccharide is selected from the group consisting of hyaluronic acid, alginate and a sulfated polysaccharide such as a glycosaminoglycan. According to a more specific embodiment the polysaccharide is selected from the group consisting of: chondroitin 4-sulfate, chondroitin 6-sulfate, dermatan sulfate, keratan sulfate, heparin, heparan sulfate, sucrose octasulfate, perlecan, syndecan, glypican and combinations thereof. According to another embodiment the polysaccharide is alginate or hyaluronic acid. According to a specific embodiment the composition comprises calcified mineral powder or particulates.

According to some embodiments the composition administered according to the present invention further comprises at least one therapeutic agent. A therapeutic agent according to the invention may include inter alia growth factors, hormones, cytokines, chemotherapeutic drugs, enzymes, anti-microbials, anti-resorptive agents and anti-inflammatory agents. According to one embodiment the composition comprises an agent known to inhibit bone-resorption and/or to enhance bone regeneration. According to a specific embodiment the agent is selected from the group consisting of: anti-resorptive agents, for example bisphosphonates, estrogen inhibitors, parathyroid hormone (PTH), fibroblast growth factor (FGF), insulin growth factor (IGF), and calcitonin. According to yet more specific embodiment, the administered composition comprises at least one bisphosphonate, including but not limited to alendronate, clodronate, etidronate, ibandronate, icadronate, pamidronate, risedronate, tiludronate and zoledronate.

According to another specific embodiment, the method of treatment or prevention comprises administering a composition comprising cells entrapped within or adhered to the peptide matrix. According to a specific embodiment, the cells are pluripotent stem cells or multipotent mesenchymal stem cells capable of differentiating to osteogenic lineages such as osteoblasts.

According to yet another embodiment the composition of the present invention serve as a carrier for modified release of at least one therapeutic agent, e.g. slow release, sustained release, and controlled release.

The composition administered according to the present invention can be dispensed in many different forms, depending on the indication and discretion of the medical practitioner. In specific embodiments the composition is a semi-fluid composition such as a gel, preferably a hydrogel referring to a three-dimensional hydrated polymeric porous matrix of bioactive nanofibers comprising amphiphilic peptides in β-sheet conformation. In other embodiments the composition is dry or a semi-dry, for example particles, granules, paste, dough, or powder, optionally obtained by lyophilization. Compositions comprising dry "hydrogel forming peptides" that will swell in aqueous environments, as well as hydrated materials are also encompassed by the present invention. In yet other embodiments the composition is fluid.

Optionally, the composition administered is sufficiently viscous to move fractured bone, such as vertebral plates of a collapsed vertebra, as it is injected. In an exemplary embodiment of the invention, injection of viscous cement contributes to fracture reduction and/or restoration of vertebral height.

The compositions may be administered by any mean capable of inserting dry, semi-dry, or semi-fluid composition to the bone. According to one embodiment the composition is administered using a device capable of inserting materials into the bone. According to one embodiment the compositions are injected using a syringe. According to a specific embodiment the compositions are administered by injection into porous or hollow bone. According to a specific embodiment the device comprises a cannula and a rod which urges the material within the cannula into the bone. According to yet another embodiment the device includes a tamping instrument, which is capable of advancement through the subcutaneous cannula.

According to one embodiment the injection is made into the hip or vertebral bone in the spine. According to yet another embodiment the injection is made into the interior of a vertebra or medullary canal of a long bone or to a bone area selected from the group consisting of compact bone, cancellous bone, epiphyseal line, epipysis, and metaphysic.

The methods of the present invention are useful for preventing and treating specific orthopedic indications wherein there is need to fill a void in a bone or a need to deliver therapeutic agents to the bone or tissue in contact with the bone. The present invention fulfills the need for pharmaceutical compositions to enhance bone repair in a mammal suffering from bone fractures, defects, and disorders which result in weakened bones such as osteoporosis and age-related loss of bone mass.

Specific osteoporosis-related conditions which can be prevented or treated by the methods of the present invention include but are not limited to: age-related osteoporosis, post-menopausal osteoporosis, glucocorticoid-induced osteoporosis, disuse osteoporosis, and scoliosis, curved upper back, back pain, spine deformation, loss of height with an accompanying stooped posture, and fractures including compression fractures.

According to some embodiments of the present invention the term "prevention" means prevention of progression of any osteoporosis-related condition.

The methods according to the present invention comprise administration of a ready-to-use pharmaceutical composition or a basic composition to which a surgeon is capable of adding any mineral, therapeutic agent or polymer according to the instant requirements of the patient in need thereof.

According to a further aspect the present invention provides a pharmaceutical composition for direct administration into deficient, deteriorated, and injured bone and low bone mineral density sites, a therapeutically effective amount of a pharmaceutical composition comprising at least one amphiphilic peptide comprising at least 2 dyads of alternating hydrophobic/hydrophilic amino acid residues, or a derivative or a salt thereof, capable of forming a β-sheet structure and promoting biomineralization, wherein the peptide comprises:
 i. 2-20 pairs of hydrophobic-hydrophilic alternating amino acid residues wherein the hydrophilic amino acid residue is selected from the group consisting of: a negatively charged amino acid, a hydroxyl-containing amino acid, and a phosphorylated-hydroxyl-containing amino acid; and
 ii. no more than 10% positively charged amino acid residues.

According to yet other aspect, the present invention provides use of at least one amphiphilic peptide comprising at least 2 dyads of alternating hydrophobic/hydrophilic amino acid residues, or a derivative or a salt thereof, capable of forming a n-sheet structure and promoting biomineralization, wherein the peptide comprises:
 i. 2-20 pairs of hydrophobic-hydrophilic alternating amino acid residues wherein the hydrophilic amino acid residue is selected from the group consisting of: a negatively charged amino acid, a hydroxyl-containing amino acid, and a phosphorylated-hydroxyl-containing amino acid; and
 ii. no more than 10% positively charged amino acid residues;
for preparation of a pharmaceutical composition for treatment, prevention or prevention of progression of osteoporosis and pre-osteoporotic condition.

Use of a pharmaceutical composition comprising at least one amphiphilic peptide comprising at least 2 pairs of alternating hydrophobic/hydrophilic amino acid residues, a derivative or a salt thereof, capable of forming a β-sheet structure and promoting biomineralization, wherein the peptide comprises:
 i. 2-20 pairs of hydrophobic-hydrophilic alternating amino acid residues wherein the hydrophilic amino acid residue is selected from the group consisting of: a negatively charged amino acid, a hydroxyl-containing amino acid, and a phosphorylated-hydroxyl-containing amino acid; and
 ii. no more than 10% positively charged amino acid residues;
for treatment, prevention or prevention of progression of osteoporosis and pre-osteoporotic condition is also within the scope of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 provides inverted-microscope observation of SaOS$_2$ cells in a 3-D hydrogel system after 14 days of incubation. A) cells on top of the hydrogel. B) cells within the hydrogel matrix.

DETAILED DESCRIPTION OF THE INVENTION

Figure 2A:
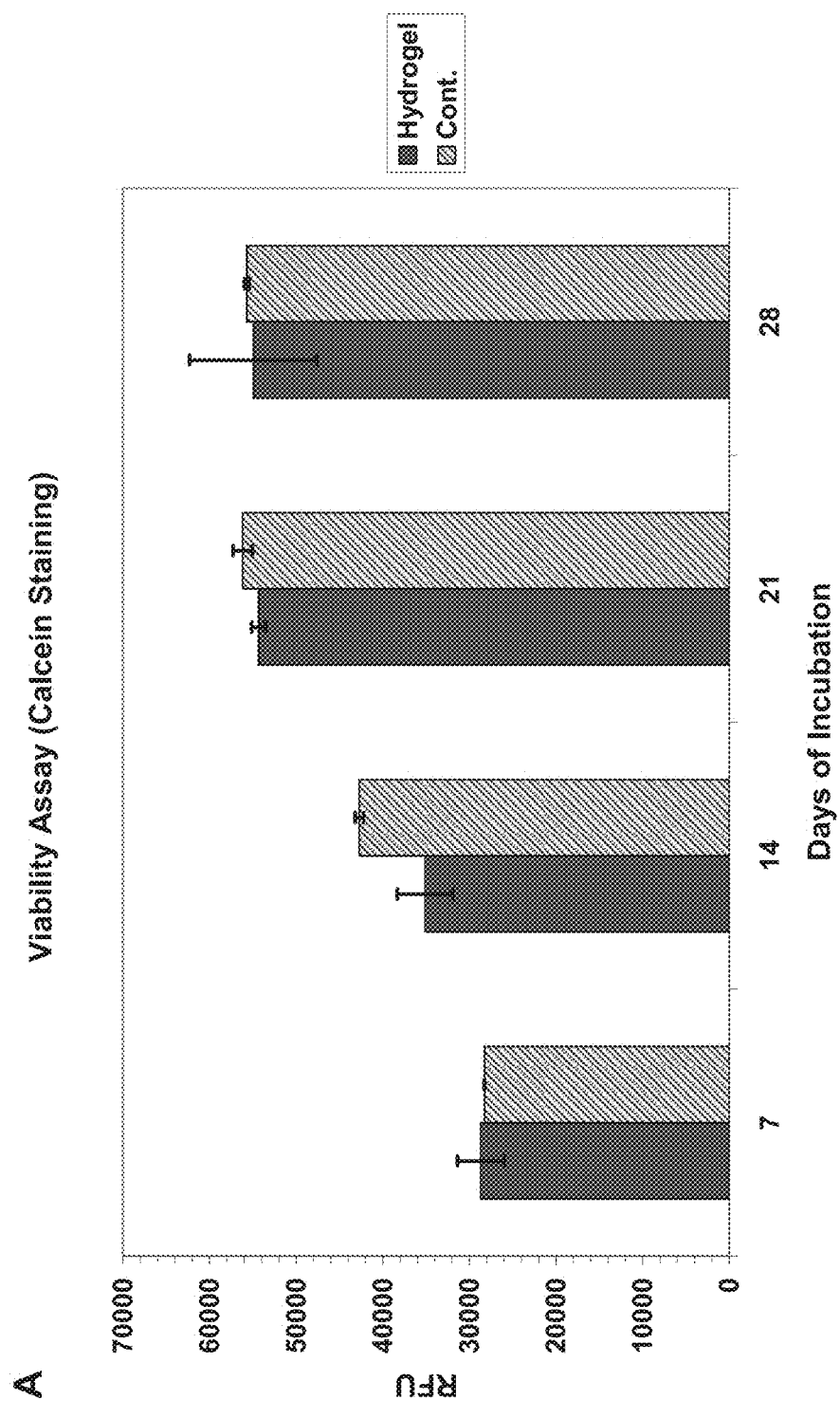
FIG. 2 shows: A) Viability of SaOS$_2$ on FD Hydrogel (calcein staining) represented by relative fluorescence units (RFU) versus days of incubation; and B) Cytotoxicity of FD Hydrogel (EthD-III Staining). Each time point reflects triplicates of cell cultures on 80 μl hydrogel.

According to the present invention amphiphilic and acidic β-sheet peptide matrices are used for direct, local, or intralesional treatment of osteoporotic bones and pre-osteoporotic conditions that are at high fracture risk. The advantages of direct treatment of osteoporotic bone using the compositions of the present invention are:
 i. The multifunctional peptides may be delivered by injection as a hydrogel, as a paste or as a powder into porous or hollow bone.
 ii. The CaP minerals loaded compositions may provide the mechanical strength required in vertebroplasty that is also beneficial to other osteoporotic bones. Else the loaded composition would be accompanied with an external bone fixation.
 iii. The composition's actively induces and expedites the local site mineralization thus bone regeneration.
 iv. Unlike PMMA (polymethyl methacrylate cement), the compositions of the present invention are biodegradable materials expected to be clarified while being replaced by the new growing bone tissue.
 v. Unlike PMMA that is a dense polymeric material the compositions of the present invention may be pre-loaded with drugs (such as bisphosphonates) that are known to enhance bone regeneration. In this manner, systemic doses of the therapeutic drugs and their side effects could be diminished.
 vi. The compositions of the present invention, comprising synthetic peptide sequences, could be conjugated during synthesis or post synthesis, with specific peptidic sequences which have been suggested to suppress osteoclast activity.
 vii. The viscosity of hydrogels is easily varied, according to the specific needs. Gels with various viscosities, or fluids can be supplied depending on their chemical and amino acid composition, the ions that may induce cross fiber interactions, mixing with other biocompatible gel forming materials, polymers, polysaccharides other proteins, on mineral loading.
 viii. The peptidic matrix provides a rich aqueous environment that is favorable for cell culture.
 ix. The matrix that is rich of acidic amino acids may attract into- or sustain within the matrix high calcium concentrations creating an environment that is favorable to cells involved in bone regeneration.
 x. The acidic and amphiphilic peptides are designed to assume a n-sheet structure that is characterized by molecular packing dimensions that have similarities to the bone mineral, hydroxyapatite.

xi. The synthetic peptides may further comprise specific amino acid sequences, for example cell binding motifs such as RGD containing sequences.

Advanced approaches in tissue engineering utilize polymer scaffolds to generate a supporting and controlled environment for tissue formation. According to the present invention a novel multifunctional peptide template matrix (PTM) was tested for direct administration into the bone and proven to be an effective and safe ingredient for prevention and treatment of bone loss and bone defects associated with osteoporosis. The PTMs according to the present invention are de-novo designed peptides, rich in acidic amino acids, amenable of assembling into beta-sheet fibers and forming hydrogels. These peptides are also capable of attracting positively charged calcium ions which are essential to bone formation. The beta-sheet structure that is characterized by dimensions that are very similar to those of HA induces the crystallization of calcium and phosphate ions en-route to HA phase.

The present invention is directed to specific medical applications of compositions comprising synthetic peptides and their matrices.

In principle, an exemplary bone repair or regenerating material will exhibit the following properties:
i. Biocompatibility: minimal toxicity to the patient and maximal similarity to natural bone;
ii. Osteoconductivity: provide a milieu amenable to recruitment, attachment, migration and proliferation of cells involved in bone growth; and
iii. Convenience: easy to use by the medical practitioner. In addition, the bone enhancing material may also exhibit the following properties:
iv. Osteoinductivity: capacity to induce regeneration or enhancement of functional bone; and
v. Biodegradability: capacity to degrade and be replaced by natural bone.

The present invention provides methods for prevention, prevention of progression and treatment of osteoporosis and related conditions by direct administration of a composition comprising peptides exhibiting the aforementioned advantageous properties. Without wishing to be bound to theory, the amphiphilic peptides disclosed herein have three primary characteristics that make them unexpectedly advantageous for prevention, prevention of progression, and treatment of osteoporosis and related conditions:
i. The peptides comprise alternating hydrophilic, mainly acidic and hydrophobic amino acids that provide the peptide with the propensity to assume a β-sheet structure, which exhibits repeating molecular distances similar to the dimensions of a HA unit cell. The β-sheet structure may also be formed by peptides that fold into (β-hairpin structure that is induced by Pro-Ala at positions i and i+1;
ii. The hydrophilic amino acids are either negatively charged (Glu, Asp) or hydroxylated (Ser, Thr, Tyr), or hydroxylated and chemically modified by a phosphate group (Ser-PO$_4$, Thr-PO$_4$, Tyr-PO$_4$). By specific patterning of these amino acids along the peptide backbone it is possible to perfect the apparent pKa of the peptide, the Ca$^{+2}$ attraction to the peptide template, and also to position the Ca$^{+2}$ binding amino acids (i.e. all the above mentioned amino acids, excluding the hydroxylated amino acids), at specific sites on the peptide that match specific crystalline planes of the HA lattice;
iii. The amino acid Proline (Pro) may be positioned at either or both peptide termini to induce the two-dimensional ordering in monolayers or to affect the extent of junction formation in hydrogels, of the amphiphilic molecules.

These peptides also form self-supporting three-dimensional matrices in solution by adjusting pH or ionic strength.

The peptide matrices may further be mixed with HA, tricalcium phosphate (TCP) or other calcium-phosphate (Ca/P) powder or particles and/or polysaccharides and/or with biocompatible polymers such as PGA/PLGA (poly glycolic acid/poly lactic glycolic acid, and/or phospholipids. Additionally, the peptide sequences can be chemically bound to a hydrophobic moiety, i.e. a lipid tail, or a repeat of hydrophobic amino acids. Without wishing to be bound to theory, a hydrophobic moiety may control the solubility of the peptide, make it less soluble in aqueous solution. It may also tune the peptide tendency to form fibrils and to hydrogel.

DEFINITIONS

For convenience and clarity certain terms employed in the specification, examples and claims are described herein.

The term "peptide" as used herein is meant to encompass natural, non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, either the L or D isomers may be used.

Conservative substitution of amino acids as known to those skilled in the art is within the scope of the present invention. Conservative amino acid substitutions includes replacement of one amino acid with another having the same type of functional group or side chain e.g. aliphatic, aromatic, positively charged, negatively charged. These substitutions may improve the peptide's properties. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Also included within the scope of the invention are salts of the peptides, fragments, analogs, and chemical derivatives of the peptides of the invention.

As used herein the term "salts" refers to both salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here refer also to ionic components added to the peptide solution to enhance hydrogel formation and/or mineralization of calcium minerals.

A "chemical derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order; namely, the amino acids are coupled in the peptide sequence in a reverse order to the amino acids order which appears in the native protein or in a specific peptide or analog identified as active.

The salts, analogs and the chemical derivatives of the peptides are preferably used to modify the pharmaceutical properties of the peptides insofar as stability, solubility, etc. are concerned.

A "peptide template matrix (PTM)" is used to describe a network of hydrogen bonded peptides, in monolayers, hydrogels, membranes or an intermediate form. The term "peptide template matrix" also refers to molecular templates that provide 2-dimensional ordered structures, that exhibit acidic functionalities at spacing compatible with biomineralization, for example with $Ca^{+2}$ positions in the planes of the HA mineral. These molecular templates may assemble into fibers that generate three-dimensional gel or non-ordered assemblies, both to which we refer as matrices.

The term "hydrogel" according to the present invention refers to a three-dimensional well hydrated polymeric porous matrix of bioactive nanofibers comprising amphiphilic peptides in β-sheet conformation. This definition includes dry "hydrogel forming peptides" that will swell in aqueous environments, as well as water-swollen materials. A hydrogel according to the present invention can be tailored to possess a range of properties depending on the peptides of which the hydrogel is composed and on additional materials which may be added such as, mineral solutions or aggregates, polysaccharides, active ingredients, exepients and more.

The term "amphiphile" refers to a molecule, in this case a synthetic peptide, possessing both hydrophilic and hydrophobic nature. A compound with such properties is called "amphiphilic".

"A pre-loaded composition" according to the present invention encompasses compositions in which substances as minerals and polysaccharides are added to the peptides prior to the formation of hydrogels or other PTMs, and also encompasses compositions in which the additional substances are added to the already formed hydrogels or other PTMs.

The term "biocompatible" as used herein refers to materials having affinity with living tissues, low toxicity and no unacceptable foreign body reactions in the living body. For example, the peptides and peptide matrices of the present invention are biocompatible.

Osteoporosis according to the present invention include all types of osteoporosis and pre-osteoporosis, osteopenia, conditions including but are not limited to: age-related osteoporosis, post-menopausal osteoporosis, glucocorticoid-induced osteoporosis and disuse osteoporosis.

The term "osteoconductive" as used herein refers to materials that provide a microenvironment that is advantageous to the healing of diseased or damaged bone. Preferably, the composite of the invention provides a milieu that is advantageous to the infiltration and proliferation of cells involved in the process of bone repair.

Bone mineral density (BMD) test measures the density of minerals in bones using Dual-energy X-ray absorptiometry, (DEXA), computed tomography (CT) scan, or ultrasound.

Direct administration according to the present invention refers to localapplication and delivery of the pharmaceutical compositions to the deficient, deteriorated or injured bone.

This term "implantation" refers to the insertion of the composition of the invention into a subject, whereby the peptide or matrix comprising a peptide of the invention or an implant comprising the peptide of the invention serves to replace, fully or partially, tissue that has been damaged or removed. Another aspect of implantation is also taken to mean the use of the composition as a vehicle to transport therapeutic agents to a certain site in a patient. In this aspect there is also included the incorporation into the composition or implant of a therapeutic agent selected from growth factors, cytokines, chemotherapeutic drugs, enzymes, anti-microbials, anti-inflammatory agents.

A subject according to the present invention is preferably a mammalian subject, and more preferably a human subject.

The term "injection" refers to the insertion of a composition of the invention into a mammal using a syringe or other device, which allows administration of the peptide composition directly to the site of treatment. Another aspect of injection is also taken to mean the use of the composition as a vehicle to transport therapeutic drugs and therapeutic agents to a certain site in a patient. In this aspect there is also included the introduction into the composite of a therapeutic agent selected from growth factors, cytokines, enzymes, anti-microbials, anti-inflammatory agents and chemotherapeutic agents such as anti-cancer drugs.

The term "physiologically acceptable carrier" or "diluent" or "excipient" refers to an aqueous or non-aqueous fluid that is well suited for pharmaceutical preparations. Furthermore, the term "a pharmaceutically acceptable carrier or excipient" refers to at least one carrier or excipient and includes mixtures of carriers and or excipients.

The term "therapeutic" refers to any pharmaceutical, drug or prophylactic agent which may be used in the treatment (including the prevention, prevention of progression, diagnosis, alleviation, or cure) of a malady, affliction, disease or injury in a patient.

The term "prevention" according to the present invention includes prevention of progression of any osteoporosis-related condition and specifically prevention of osteoporosis-related fractures. The term "treatment" relates to any existing osteoporosis-related condition.

Biomineralization

The term "biomineralization" refers to the deposition of inorganic solids in biological systems. Biomineralization has been defined as the highly regulated process that produces materials such as bones, shells and teeth that have specific biological functions and structures. These and similar biologically controlled materials are characterized by specific crystallographic and chemical properties, which include: rather uniform particle size, well-defined structures and compositions, high level of spatial organization, preferred crystallographic orientation and higher order assembly into hierarchical structures (Mann, 2001). Biomineralization may take place within four main biological sites: on the cell (epicellular), in the space between closely packed cells (intercellular), inside the cell (intracellular) and within insoluble macromolecular framework outside the cell (extracellular). In general, two types of assembled organic structures are used to delineate the mineralization sites: lipid vesicles within the cell and macromolecular frameworks outside the cell. Intercellular biomineralization usually takes place within vesicles that form controlled microenvironment for nucleation. However, large bone structures are constructed in the extracellular region, where biomineralization is regulated through the activity of specialized cells that seal off a space into which an organic matrix, consisting of insoluble proteins and polysaccharides, is secreted. This complex of macromolecules, or organic matrix, serves as a template that controls the nucleation process through an inorganic-organic interface (Boskey, 1998; Weiner, 1997; Mann, 1988). In general, this organic matrix can be divided into two classes of macromolecules; a) framework, insoluble fraction of the bone organic matrix, which is primarily collagen; and b) acidic polypeptides and polysaccharides, proteoglycans, glycoproteins.

"Nucleus" as used herein, refers to clusters of ions of nanoscale dimensions, which resemble a small piece of the bulk crystalline phase. There is little structural information about the initial states formed in mineral precipitation. The nucleus comprises strongly interacting ions so that the particulate energy overcomes solvation and surface energy. Although ions in the nuclei are relaxed to some degree from their normal unit cell positions there is still close correspondence between the lattice parameter of the nucleus structure and the bulk mineral phase.

The term "homogeneous nucleation" refers to spontaneous formation of nuclei in a supersaturated solution. The term "heterogeneous nucleation" refers to the formation of nuclei on the surface of a substrate present in crystallization medium. Homogeneous nucleation occurs due to thermodynamically driven, spontaneous formation of nuclei in supersaturated solutions. Heterogeneous nucleation is initiated with the formation of nuclei on a substrate surface that is present in an aqueous medium. Heterogeneous nucleation occurs at lower saturation levels than those required for homogeneous nucleation since the presence of an external substrate can significantly reduce the interfacial energy created along with the nuclei formation. In heterogeneous nucleation, nuclei are stabilized by attachment to a foreign surface particularly if there is chemical and structural complimentary.

Biomineralization is controlled by chemical, spatial and structural mechanism, for example:
a) Chemical control is related to the type of functional groups (carboxyls, phosphate) that tend to bind to the growing crystal or nuclei. It is also related to the solubility product (Ksp) that is crucial for determining the thermodynamic limit for precipitation of ionic materials. Precipitation occurs when ion concentrations in solution are greater than their Ksp equilibrium value. The difference between ion concentrations in solution and in equilibrium determines the degree of saturation of the solution. An increase in supersaturation rapidly increases the thermodynamic driving force for precipitation since it decreases the activation energy for nucleation.
b) Spatial control is the regulation of size and shape of biominerals by restricting the deposition to define spaces such as organic frameworks.
c) Structural control, or epitaxis, enables nucleation of a certain face on an insoluble crystalline substrate, the organic matrix interface, and is associated with the concept of lattice matching.

Biomineralization and Organic Matrices

The two main properties of organic interfaces that lead to specificity in nucleation of biominerals are electrostatic accumulation (attraction of inorganic ions to binding sites at the organic matrix), and structural correspondence (specific arrangement of the matrix to control orientation, size and morphology of the growing crystal). Electrostatic accumulation is considered to be the initial step in biomineralization. It is believed that the bone acid-rich proteins and possibly also collagen control nucleation via charged amino acids on their surfaces. Without wishing to be bound to theory, the acidic and phosphorylated amino acids, which at biological pH, expose charged functional groups, i.e. negatively charged carboxylate groups of glutamic acid and aspartic acid as well as negatively charged phosphates. (Addadi, 1985; Mann, 1988) are involved in binding $Ca^{+2}$ ions and in initiating the mineralization process.

β-Sheet Self Assemblies

DeGrado and Lear (1985) showed that amphiphilic peptides comprising repetitive dyads of hydrophilic and hydrophobic amino acid residues tend to self assemble into β-pleated sheet structure at air-water interfaces. The assembly of β-sheet peptides into one-dimensional (1D) ribbons is mediated by inter-strand hydrogen bonds along the direction that is normal to the peptide strand. The flexibility of the peptide backbone and the repetitive nature of the hydrophilic-hydrophobic amino acid motif may induce dislocation defects that inhibit the 2D ordered structure. The present inventor and others (Rapaport, 2000) obtained 2D order β-strand assemblies at air-water interfaces by using peptides terminated with proline (Pro) residues. Pro was chosen to be the terminal amino acid since it is a potent disrupter of β-sheet structure. Without wishing to be bound to theory, Pro termini minimize free motion and dynamic disorder at the ribbon edges due to geometric constrains imposed by the cyclic side chains. The electrostatic interactions between the chain termini contribute to juxtaposition of the β-sheet ribbons.

It was shown that peptide sequences comprising alternating hydrophilic-hydrophobic amino acid repeats where the hydrophilic amino acids are negatively charged can form hydrogels and other matrices and that these matrices are useful in the formation of calcium phosphate mineralization, it is now shown that pharmaceutical compositions comprising these matrices are useful for direct administration into the bone for prevention of progression and treatment of osteoporosis and related conditions.

Without wishing to be bound to theory, a repetitive β-sheet structure i.e. 4.7 Å and 6.9 Å, are in excellent correlation with HA crystal unit cell dimensions, a=b=9.432 Å and c=6.881 Å. Accordingly it is evident that calcium ions in HA lattice are positioned at distances that match characteristic distances in β-sheet. The 9.432 Å axis is twice the distance of ~4.7 Å, thus there is a match between calcium ions along a/b axes and hydrophilic amino acids in every second β-strand. The 6.881 Å along the c axis equals the distance between hydrophilic amino acids along a β-strand.

The crystal growth of calcium phosphate species in solution may occur via sequential modifications of intermediate amorphous or ordered phases. It is possible that amorphous phases will first precipitate followed by the formation of minerals with decreasing solubility.

Other than HA, several other Ca/P phases have been identified as intermediates in the biomineralization of Ca/P (Mann, 2001). Furthermore, it was found that Ca/P phases in aqueous solutions mainly include octacalcium phosphate (OCP) and dicalcium phosphate dehydrate (DCPD) (Iijima, 1998). Since hydroxyapatite is considered the most thermodynamically stable in physiological environment, and OCP and DCPD are kinetically favorable, they are regarded as metastable phases of Ca/P (Iijima, 1998) that transform over time to the thermodynamically stable form of hydroxyapatite.

Matrix Preparation

The peptides, fragments, derivatives and analogs thereof, are preferably synthesized using conventional synthesis techniques, e.g., by chemical synthesis techniques. These methods include exclusive solid phase synthesis, partial solid phase synthesis methods, fragment condensation, classical solution synthesis. Solid phase peptide synthesis procedures are well known in the art and described for example by John Morrow Stewart and Janis Dillaha Young, Solid Phase Peptide Syntheses (2nd Ed., Pierce Chemical Company, 1984). A skilled artesian may synthesize any of the peptides of the present invention by using an automated peptide synthesizer using standard chemistry such as, for example, t-Boc or Fmoc chemistry. Synthetic peptides can be purified by preparative high performance liquid chromatography as known in the art and the composition of which can be confirmed via amino acid sequencing.

Alternatively, the peptides and other constructs of the present invention may be prepared by known recombinant DNA techniques by cloning and expressing within a host microorganism or cell a DNA fragment carrying a coding sequence of the selected peptide or construct. Such techniques were described for example, by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Coding sequences for the peptides can be prepared synthetically, or can be derived from viral RNA by known techniques, or from available cDNA-containing plasmids.

According to one embodiment of the present invention the pharmaceutical composition further comprises at least one therapeutic agent. A suitable therapeutic agent can be selected from the group consisting of antibiotics, antiviral agents, chemotherapeutic agents, anti-rejection agents, analgesics and analgesic combinations, anti-inflammatory agents, hormones, growth factors and cytokines. Any additives to the composition may be added at any time, including during preparation of the composition or before, during or after administration to the subject.

The compositions administered according to the methods of the present invention further comprise peptides, proteins and other substances having osteogenic activity which are linked to or mixed with the amphiphilic peptides. An exemplary family of osteogenic peptides is described in U.S. Pat. No. 7,163,920. Other active substances known to enhance bone and cartilage repair are angiotensinogen, angiotensin AI and its fragments and analogs, angiotensin AII and its fragments and analogs, bone morphogenic protein-2, bone morphogenic protein-4, bone morphogenic protein-6, bone morphogenic protein-7, transforming growth factor-beta, insulin-like growth factor, and parathyroid hormone (PTH).

Cellular tissue matrices may be prepared by removing cellular components form tissue via mechanical and chemical manipulation and mixing with the composition of the present invention to produce cellular matrices by methods known in the art.

According to one embodiment of the present invention a biocompatible polymer or mixture thereof is incorporated in the pharmaceutical composition administered according to the methods of the present invention. Suitable polymers include natural and synthetic polymers. Examples of natural biocompatible polymers include polysaccharides and oligosaccharides. According to one embodiment of the present invention the natural biocompatible polymer is a polysaccharide, preferably hyaluronic acid, alginate or a sulfated polysaccharide such as a glycosaminoglycan selected from the group consisting of chondroitin 4-sulfate, chondroitin 6-sulfate, dermatan sulfate, keratan sulfate, heparin, heparan sulfate, sucrose octasulfate, perlecan, syndecan, glypican and combinations thereof. Heparin is meant to encompass the various derivatives of heparin including very low molecular weight heparin, low molecular weight heparin, heparan, and heparin mimetics. Hyaluronic acid is meant to encompass cross-linked and non-crosslinked hyaluronic acid derivatives. Additional natural biocompatible polymers include starch, collagen, gelatin, glycogen, chitin, cellulose, keratins or combinations thereof. The polysaccharide improves the hydrogel's chemical and rheological properties.

Synthetic polymers include non-biodegradable or biodegradable material. Examples of non-biodegradable materials include polytetrafluoroethylene, perfluorinated polymers such as fluorinated ethylene propylene, polypropylene, polyethylene, polyethylene terapthalate, silicone, silicone rubber, polysulfone, polyurethane, non-degradable polycarboxylate, non-degradable polycarbonate, non-degradable polyester, polyacrylic, polyhydroxymethacrylate, polymethylmethacrylate, polyamide such as polyesteramide, and copolymers, block copolymers and blends of the above materials.

Examples of biodegradable materials include hydrolyzable polyesters such as polylactic acid and polyglycolic acid, polyorthoesters, degradable polycarboxylates, degradable polycarbonates, degradable polycaprolactones, polyanhydride, and copolymers, block copolymers and blends of the above materials.

The composition may be sterilized for use in vivo, in particular for use in clinical and therapeutic applications in mammals Fractures and other defects in long bones heal via a process known as endochondral ossification while defects and lesions in intramembranous bones heal via an osteogenic route. Four stages of fracture repair have been characterized (reviewed in Bolander, 1992). Stage 1 is the immediate injury response; stage 2 marks the synthesis of new bone matrix and callus formation in a process termed intramembranous ossification; stage 3, designated chondrogenesis, occurs as the mesenchymal cells develop into chondrocytes and are eventually replaced by cartilage; stage 4 is the formation of bone from cartilage in a process known as endochondral ossification. According to the principles of the present invention the peptide matrices comprise therapeutic agents that have the capacity to act at some or all of the stages in order to enhance bone regeneration, repair, reduce inflammation or infection and ensure the formation of functional bone.

According to the principles of the present invention the peptides and compositions of the invention are useful in indications where due to osteopenia or osteoporosis conditions bone enhancement, bone substitution and bone healing is desired. Types of bone that can be treated by the method of the present invention include but are not limited to trabecular bone, and cortical bone. Specific bones that can be treated by the present invention include the clavicle, scapula, humerus, ulna, radius, ilium, sacrum, vertebrae, hip bone, femur, fibula and tibia.

The following examples are intended to be merely illustrative in nature and to be construed in a non-limitative fashion. Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

EXAMPLES

The following examples demonstrate design, characterization, production, in vitro assaying and in vivo efficacy and safety of hydrogel compositions comprising peptides rich in acidic amino acids at physiological pH. The experiments demonstrate induction of HA nucleation during formation of HA-composite-hydrogels, formation of hydrogels amenable to 2-D and 3-D cell culture which support cell adhesion and proliferation that are expected to be beneficial to local treatment of osteoporetic bones, in particular with hydrogels that would be designed to enhance osteoblasts activity and suppress bone resorption by osteoclasts. In vivo assays for assessing bone regeneration activity, safety, compatibility and non-immunegenicity are also presented.

Example 1

Peptide Synthesis

The peptides were synthesized by conventional solid phase synthesis methods, using either tBOC or FMOC chemistry. The peptides of the invention may further be prepared using recombinant DNA techniques known in the art.

Example 2

Preparation of Peptide Hydrogel

According to a specific example the matrix is formed in the following way: dissolving the peptides at high pH (above about pH 8) using either buffer (Tris) or NaOH. With the addition of the peptide the pH of the mixture drops and hydrogel is formed. The peptide that is dissolved in alkaline solution may also be titrated with HCl to a pH ~7 to form a gel. The same can be done with HA or other mineral particles incorporated in the first step (low pH). Upon gelation the particles get trapped in the gel.

Example 3

In vitro Biomineralization

In vitro biomineralization was performed with monolayer peptide films deposited on SBF1.5 solution (×1.5 ionic profile of blood serum Tris buffered to pH 7.35; $Na^+$ 213.0, $K+$ 7.5, $Ca+2$ 3.8, $Mg+2$ 2.3, $HCO3-$ 6.3, $Cl-$ 223.0, $HPO4-$ 1.5, $SO4-2$ 0.75 mM). Minerzlization was also obtained on hydrogels that were in contact with SBF1.5 solution.

A considerable amount of work has been done in-vitro in order to decide whether acidic amino acids are indeed effective in HA formation. Usually these studies are done by exposure of surface active material to ionic solution followed by evaluation of HA nucleation degree on this surface. Ionic solutions, in which nucleation occurs, have a few variables such as, minerals components and their concentrations, buffer capacities, pH, temperature and preparation procedures. The two essential components of SBF1.5 are calcium and phosphate. The solution was prepared according to the prototype-SBF procedure developed by Kokubo (1990).

Simulated Body Fluid (SBF): The SBF consists of ion concentrations ($Na+$ 142.0 nM, $K+$ 5.0 mM, $Mg^{2+}$ 1.5 mM, $Ca^{2+}$ 2.5 mM, $Cl-$ 147.8 mM, $HCO3-$ 4.2 mM, $HPO_4^{2-}$ 1.0 mM, and $SO_4^{2-}$ 0.5 mM) similar to those of human blood plasma. However there are different versions of SBF as well as differences in saturation degrees. In one non-limiting example, reagent grade NaCl, $NaHCO_3$, KCl, $K_2HPO_4$, $MgCl_2$, $CaCl_2$ and $Na_2SO_4$ are dissolved in $ddH_2O$, Next, about ~50 ml of 1M HCl are added to the solution in order to prevent the precipitation of the next added salt, $CaCl_2$.

After the addition of all the salts, the pH of the solution was adjusted to ~7.35 by adding Trizma base (6 mM) and HCl at 37° C.

Example 4

In Vivo Biomineralization

A peptide matrix is prepared according to example 2 above. The matrix is injected into a defect created in a bone of an animal. The peptide is delivered as a gel or gel with TCP or HA particulates.

Example 5

Cell Proliferation Assay

The proliferation of osteoblasts on an implant prepared according to Example 3 is tested. Proliferation is observed using PCNA staining or $^3$H-thymidine uptake. In one experiment, human osteoblasts ($10^4$-$10^6$ cells/100 ul) are grown on implants in microwell plates.

Example 6

Hydrogel Formation

Four peptides were tested for their tendency to form hydrogels as function of pH and $Ca^{+2}$ ion concentrations. The peptides are 13 amino acids long having the sequence P—Y-(Z-Y)$_n$-P, wherein n=5 and Y and Z are alternating hydrophilic (Y) and hydrophobic (Z) amino acids:
1. $P_{FD}$-13-PD(FD)$_5$P
2. $P_{FE}$-13-PE(FE)$_5$P
3. $P_{LD}$-13-PD(LD)$_5$P
4. $P_{LE}$-13-PE(LE)$_5$P The experiment goal was to find appropriate conditions for hydrogel formation at physiological pH values (~7.2) assuming that the type of amino acids in the dyads will determine the propensity of the system to form hydrogles thus the pH and the $Ca^{+2}$ ionic concentration of the system.

In an alkaline solution the acidic amino acid side chains tend to be negatively charged. Under these conditions charge-charge repulsive forces keep the peptides dissolved in solution. Upon lowering the pH the peptides which become uncharged undergo self-assembling through inter-strand hydrogen bonding, to form fibrous structure that stabilizes highly hydrated-gel, hydrogel. Table 1 demonstrates the differences in peptide propensities towards hydrogel formation. All the peptides were dissolved in 0.1 M NaOH solution (pH 13) to 4% weight per volume (w/v). All the peptides lowered the pH of the solution to about 6-8. Peptide $P_{LE}$-13 formed self-supporting hydrogel at neutral pH.

TABLE 1

Hydrogel formation from 4% w/v peptide dissolved in 0.1M NaOH solution.

| Peptide name | Peptide concentration (M) | Final pH | Form of product Liquid −/gel + |
|---|---|---|---|
| $P_{LD}$-13 | 0.027 | 6 | − |
| $P_{LE}$-13 | 0.025 | 7 | + |
| $P_{FD}$-13 | 0.024 | 8 | − |
| $P_{FE}$-13 | 0.023 | 8 | − |

Two main factors appear to govern the behavior of the systems described in table 1, the differences in their molar concentrations and the type of amino acid dyads. The peptide $P_{LD}$-13 with the highest molarity (0.027M) acidified the solution down to pH ~6 with no appearance of gel phase. The peptides with the lower molarity $P_{FD}$-13 (0.024M) and $P_{FE}$-13 (0.023M) dropped the pH of the NaOH solution to ~8 with no gel formation. The peptide $P_{LE}$-13 (0.025M) lowered the pH to ~7 and formed a gel. It is reasonable to assume that the lower the pH the higher the probability of the peptide to form a gel. Nevertheless, $P_{LD}$-13 (0.027M) which lowered the pH to ~6 remained fluid whereas $P_{LE}$-13 (0.025M) did assemble into a hydrogel. This difference in the behavior of the two peptides, is attributed to the higher tendency of the glutmaic acid to form inter-strand hydrogen bonds, as compared to the side chain of aspartic acid which are shorter and thus more limited in their ability to form stabilized network of hydrogen bonds. This difference between the $P_{LE}$-13 $P_{LD}$-13 behaviors demonstrates the important effect amino acids side chains may have on tuning hydrogel formation and properties. This experiment also demonstrated for the first time that PTMs may form hydrogels at physiological pH values.

Noteworthy, The carboxyl groups of the Glu and Asp side chains have intrinsic pKa values of 4.3 and 3.9, respectively. Accordingly, at the pH the $P_{LE}$-13 hydrogel formed, the glutamic acid side chain should have been deprotonated. Nevertheless, it is unreasonable that a charged structure would form a stable assembly like a hydrogel. This result goes along with previously reported studies on glutamic acid rich peptides that noted a positive shift in their observed pKa values (Rapaport et al. 2000 and references therein). Aspartic acid side chains probably have lower propensity towards stabilizing the beta-sheet structure therefore $P_{LD}$-13 which reduced the pH value down to ~6 did not yield a hydrogel. The Influence of Amino Acid Hydrophobicity on Hydrogel Formation In the next set of experiments the hypothesis that the more hydrophobic side chains would stabilize the beta-sheet fibril thus hydrogel formation, at higher pH values, was tested. Table 2 summarizes the effect of the hydrophobic side chain on the pH at which hydrogel is obtained. $P_{FE}$-13, $P_{FD}$-13, $P_{LE}$-13 and $P_{LD}$-13 were dissolved in different NaOH solutions to the same molar concentration (0.023M).

TABLE 2

The final pH values (+/− 0.5 pH units) obtained by dissolution of 0.023M PTMs in NaOH solution of concentrations indicated in the first column.

| NaOH M | pH | $P_{FE}$-13 | $P_{FD}$-13 | $P_{LE}$-13 | $P_{LD}$-13 |
|---|---|---|---|---|---|
| 0.01 | 12.0 | 5.5 | 5 | 5 | 4.5 |
| 0.05 | 12.7 | 6.5 | 7 | 6.5 | 5 |
| 0.07 | 12.8 | ** | 7 | 7* | 6 |
| 0.08 | 12.9 | >7.0 | 7.5 | 7 | 7.5 |
| 0.10 | 13.0 | 8.0 | 8.5 | 8 | 8.5 |

The mixtures that result in hydrogel formation are marked by gray background.
*$P_{LE}$-13 in 0.07M NaOH gelled over night.
** There's no need to perform this experiment since the gel forms even at higher pH's.

The results of this experiment show that the peptide $P_{FE}$-13 with the more hydrophobic side chains (F) stabilized a hydrogel even at pH>7 whereas the peptide with the less hydrophobic (L) amino acid $P_{LE}$-13 requires pH ~6.5 to stabilize a hydrogel. Peptide $P_{LD}$-13 forms hydrogel at lower pH compared to that of $P_{FD}$-13 which also forms a hydrogel, like $P_{FE}$-13, at pH ~7.

The Effect of Ca+2 Ions on Hydrogel Formation

The next set of experiments (Table 3, peptide final concentration 1.34% weight) demonstrates the effect of calcium ions on the pH at which hydrogels may be obtained. With the addition of $Ca^{+2}$ ions to the solution of the peptide the system may form a hydrogel. These hydrogels are obtained at peptide concentrations smaller and at pH values higher than those without the ions. This result is explained by the stabilizing effect $Ca^{+2}$ may have on the negatively charged carboxylate groups. It is possible that the $Ca^{+2}$ may also induce cross linking between strands in a mechanism similar to that of alginate hydrogel formation. The concentration of $Ca^{+2}$ ions in the hydrogel are a few times larger than in the body serum (2.5 mM). This is envisaged to yield a better environment for the bone forming osteoblast cells. In any event, the $Ca^{+2}$ provides an additional parameter to control the hydrogel rheological and stability properties.

Peptides, 2% (w/v) in the liquid state were dissolved in 0.05 M NaOH to yield 7.0<pH<7.5 solution. Upon addition of 60 μl of 60 mM (or up to 100 mM) calcium chloride solution, all peptides formed a hydrogel over a period of several minutes, with the exception of $P_{LD}$-13, which gelled partially over hours.

TABLE 3

The possible effect of $Ca^{+2}$ ion on the PTM hydrogel pH.

| Peptide | Conc. mM | pH mother solution | Hydrogel formation (✓) upon the addition of $CaCl_2$ sol. $Ca^{+2}$ final concentration mM indicated | | | | |
|---|---|---|---|---|---|---|---|
| | | | 6.7 | 13.3 | 20 | 27 | 33 |
| $P_{FE}$-13 | 0.0077 | 7.5 | | | ✓ | ✓ | ✓ |
| $P_{FD}$-13 | 0.0081 | 7.5 | | | | ✓ | ✓ |
| $P_{LE}$-13 | 0.0086 | 7.2 | | | ✓ | ✓ | ✓ |
| $P_{LD}$-13 | 0.0091 | 7.0 | | | * | * | * |

* partial formation of hydrogel over hours.

Rheology Measurements

The viscoelastic properties of $P_{FE}$-13 (4% w/v) hydrogel at pH=5 were measured. The high G' storage modulus value, ~3000 Pa on first sweep, indicates gel that is relatively stiff compared to rheology properties of previously reported peptides.

Forming Composite Ha-PTM Hydrogels

The inclusion of HA particles in hydrogels is expected to provide both a supportive environment for osteoblasts and also mechanical strength.

The Induction of Ha Formation on Peptide Template Monolayers

Monolayers of peptide $P_{FD}$-13 were incubated over SBF1.5 solution (simulated body fluid that is 1.5 times more concentrated in ion concentration compared to human blood serum). Results of Langmuir isotherms, FTIR spectra and EM images and diffraction indicate that the peptide monolayer accelerates the formation of HA compared to several controls that were tested (EM grid, ZnSe prism). The induction of HA formation is also demonstrated in the 3-D hydrogel system by optical phase microscope image and IR spectra. As described in OU-YANG et al. 2000, the peak at ~1063 $cm^{-1}$ may be deconvoluted into peaks at ~1038 and ~1070 $cm^{-1}$ where the first corresponds to apatitic phosphate and the second to free phosphate.

Example 7

In Vitro Cell Culturing on Hydrogels a. The Stability of the Hydrogels to Cell Culture Conditions The first set of experiments examined the stability of different hydrogels to gamma irradiation (5000 rad), incubation conditions (37° C.; humidity and $CO_2$ atmosphere) and cell media addition without cells.

The hydrogels were stable to gamma irradiation and incubation conditions. As for the medium, it was rapidly taken up by the hydrogels which got swollen. The addition of liquid to the hydrogels has to be done gently as it happened that the gel disintegrated upon excessive soaking in media. The pH of the hydrogels remained stable under the experimental conditions.

b. The Human Osteosarcoma Cell Line SaOS-2 System

In-vitro experiments are performed for examining the PTM hydrogel potency as a multifunctional bone restoring and regeneration agent. The experiments screen different peptides and different additives to hydrogels, and find formulations optimized with respect to supporting osteoblastic cell viability. It is expected that osteoblastic cells will function better in a three dimensional, tissue-like environment. Nevertheless two-dimensional hydrogel systems that are easier to generate and study have also been studied. $SaOS_2$ cell line was chosen to demonstrate the ability of bone cells to undergo proliferation and bio-mineralization in/on the hydrogel scaffold, these human cells which mineralize in culture have been well-characterized with respect to expression of osteoblastic traits. In-vitro experiments were also conducted to evaluate the applicability of the hydrogel for cell cultures and tissue engineering applications. Jayawarna et al. (2006) used chondrocyte cell culture in/on self-assembled Fmoc-dipeptide hydrogel scaffolds; Silva et al. (2004) used their artificial nanofiber scaffolds to induced rapid differentiation of neural progenitor cells into neurons; Zhang 2003, and Holmes et al. 2000, described the use of octapeptides and hexadecapeptides to generate highly hydrated gels for cultures of nerve cells, endothelial cells, and chondrocytes.

The results on qualitative and quantitative evaluation of cell viability and proliferation of cell-cultures grown on thin films of hydrogels (two dimensional, 2D systems) and within bulk hydrogels (three-dimensional, 3D systems) are described.

b1. 2D System

The cells were maintained in Dulbecco's modified Eagle's medium (DMEM) supplemented with 10% fetal calf serum (FCS), 100 mg/ml streptomycin, 100 U/ml penicillin and 2 mmol/L L-glutamine. Cells were maintained at 37° C. in a humidified atmosphere containing 5% $CO_2$. Cell suspensions of the SaOS-2 cells were obtained after trypsin treatment. In 2D cultures the cells were seeded on top of the different hydrogels. Since the cells are almost transparent and the hydrogels are either opaque or, polarizing the light, the visualization of the cells viability under the microscope is difficult. In order to overcome this problem different cell coloring techniques, such as Tripan-blue (TB); Methylen-blue (MB); Almar-blue (AB); Neutral-red (NR); Hematoxylin-eosin (HE), were used. Some of the techniques were found toxic (MB, NR); others (TB, AB) did not improve visualization, and the HE technique requires fixation prior to coloring. With any of these techniques the cultures were seized.

The visualization of cell viability became possible using a very thin layer of hydrogel (<1 mm). The system is prepared by aliquoting 100 μl of liquid hydrogel onto a 22 mm cover slip (in a 30 mm Petri-dish). Subconfluent cells were harvested by trypsinization, counted, and diluted in the cells media to $3*10^5$ cells/ml. 50 μl of cell suspension were then pipette over the hydrogel. Cells were allowed to reside undisturbed in the incubator for 1 hr, after which 250 μl of culture media were added to the Petri-dish. Plates were then transferred to incubation for various periods of time. For control uncoated cover slips were seeded in the same manner. The seeding density of $SaOS_2$ was ~3800 cells/cm$^2$ and culture medium was exchanged twice a week.

The results demonstrate that the hydrogels FD, FE and LE can provide a proper environment for cell adhesion spreading and proliferation. Furthermore, cell division on these hydrogels has been observed.

b2. Three Dimensional (3D) Cell Culture in PTM Hydrogels

In order to build a 3D cell culture system, hydrogels containing culture media were prepared. Two approaches were undertaken: In the first approach the peptide was dissolved in culture media and since this lowers drastically the pH of the medium, sodium bicarbonate was added in order to restore the physiological pH. In the second approach, hydrogel at physiological pH was formed in one step by dissolving the peptide in appropriate concentration in NaOH solution. The hydrogel that was obtained was lyophilized and subsequently rehydrated using culture media. Both approaches showed positive results in terms of cell adhesion and spreading.

In order to evaluate quantitatively the cell viability and cell proliferation in 3D systems LIVE/DEAD Viability/Cytotoxicity Kit (Molecular Probes) was used according to the manufacture's instructions.

b3. Qualitative Results in 3D System

Inverted-optical microscope: FIG. 1 shows differences in cells that appear to be spread on the hydrogel upper surface (A) and cells that are entrapped within the hydrogel matrix (B). Both images in FIG. 1 were taken from the same spot of the hydrogel, whereas only the focus of the image was different thus the images reflect different heights within the gel.

Confocal-microscope: Cells that were incubated in a 3D matrix for 14 days were stained with LIVE/DEAD kit. The cell seeded hydrogel was set on a glass slide and visualized in a confocal-microscope at ×660 using laser light that match excitation and emission wavelengths of each prob.

b4. Quantitative Evaluation Of $SaOS_2$ Growth

On 2D hydrogels: Quantitative studies of cell proliferation were performed in 2D systems of $P_{FD}$-13 (3% w/v) hydrogels that were formed with DMEM+bicarbonate at pH ~7.0 in 96-wells plates.

The plates were sterilized by gamma irradiation (5000 rad). 50 μl of culture media were pipette on top of each hydrogel for conditioning. After 1 h at room temp, $SaOS_2$ cells were seeded on top of the hydrogels. Single cell suspensions obtained after trypsinization which diluted to concentration of $1\times10^5$ cells/1 ml. 50 μl of this cell suspension was seeded on top of each hydrogel. Triplicates of none coated wells were seeded and served as control. After 1 h of incubation, medium was added to complete the volume to 200 μl in each well (20 μl in the coated wells and 150 μl in the uncoated wells). Culture medium was exchanged twice a week. Viability of the cells was evaluated every week, over a month, using the LIVE/DEAD Viability/Cytotoxicity Kit (Molecular Probes, Invitrogen, France) following the manufacturer's instructions. Briefly, samples were stained for 30 min at room temperature (in dark) with PBS containing 2 mmol/l calcein-AM and 4 mmol/l ethidium-III. Calcein-AM is a non-fluorescent cell permeant fluorescein derivative, which is converted by cellular esterase activity into cell-impermeant and highly fluorescent calcein. Calcein accumulates inside live cells having intact membranes and results in a green fluorescent signal. Ethidium-III enters dead cells with damaged membranes and undergoes a 40-fold enhancement of fluorescence upon binding to their DNA, leading to a red fluorescent signal. The plates were measured in a plate reader (calcein: Ex=495 nm, Em=515 nm. ethidium: Ex=530 nm, Em=635 nm). After measuring the medium fluorescence, the gain was set constant for each probe.

Figure 2B:
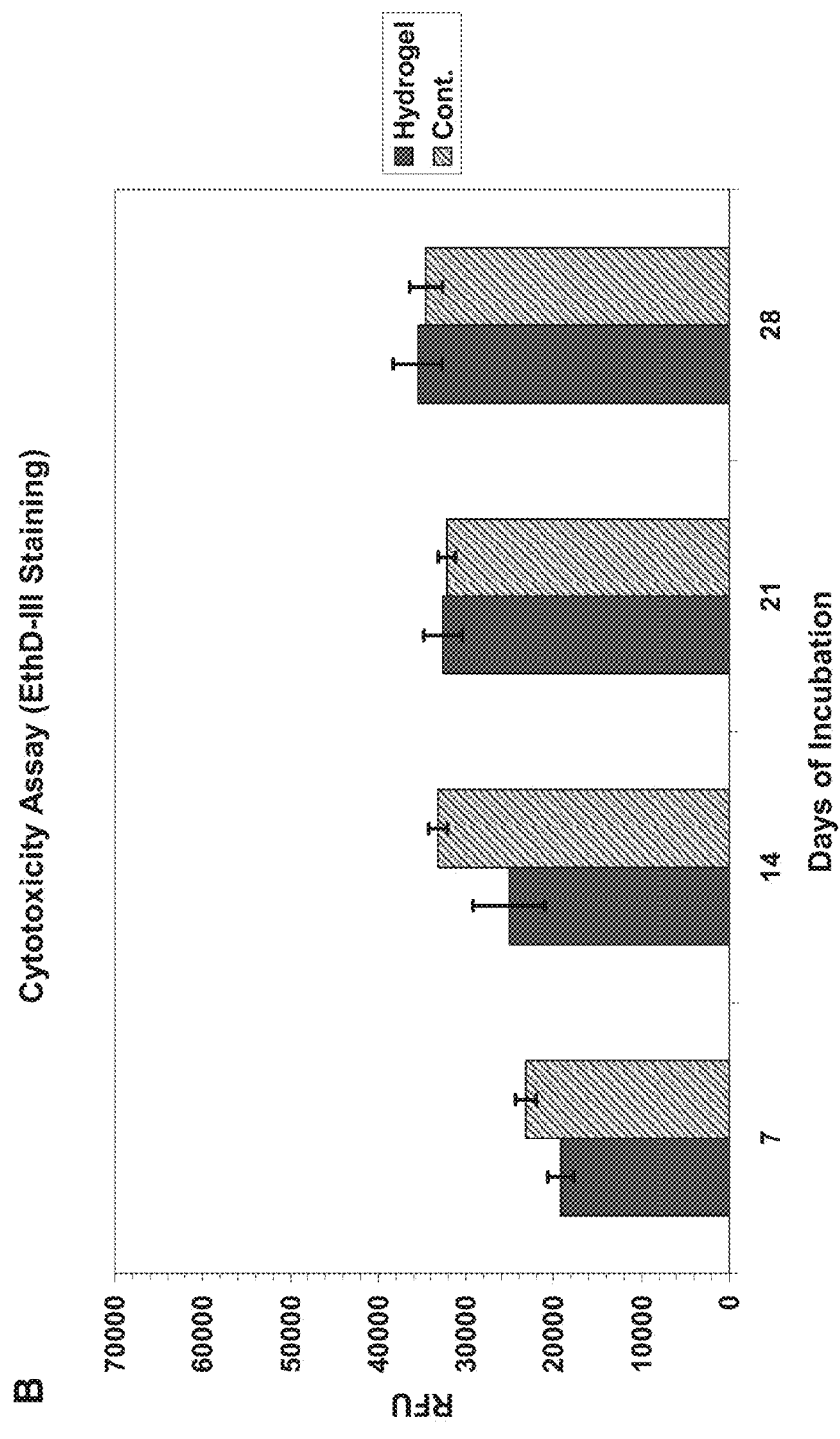

The concentration of the peptide in these experiments is lower by 1% compared to the values used in the experiments shown in the 2D assay where hydrogels were formed with NaOH solution only. Here the hydrogel is formed with a medium that contains $Ca^{++}$ and other divalent ions therefore lower peptide concentrations are needed to generate hydrogels. Triplicates of wells coated with $P_{FD}$-13 hydrogel were seeded with $SaOS_2$ cells. Uncoated wells were seeded in the same manner and served as control. The plates were incubated for different time intervals and the viability of the cells was evaluated using LIVE/DEAD kit. As seen in FIG. 2, the viability of the cells on $P_{FD}$-13 hydrogel is as good as the control samples (except for the 14$^{th}$ day). On the third week the cells appear to have entered the stationary phase. The cytotoxicity influence of $P_{FD}$-13 is not significant. The death in the control samples was even higher on the 7$^{th}$ and 14$^{th}$ days. In summary cells proliferated on $P_{FD}$-13 hydrogel is similar to that on the plate and the hydrogel is non toxic to the cells.

b4. Visualization of Cells within Peptide 3D Matrices

Figure 4:
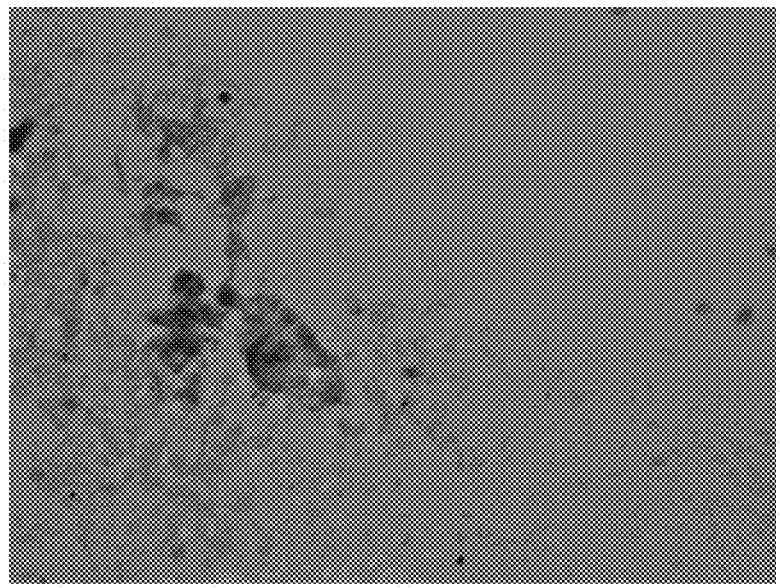
FIG. 4 Optical microscope image of a slice obtained by the cryostat technique, of 3D matrix showing SaOS2 cells (darker objects) within the fibers of the hydrogel.

This assay exemplifies the possibility of using the hydrogel as a three dimensional matrix supporting growth of bone cells. Cells were incubated in 3D hydrogels for 15 days and stained with live/dead kit. The hydrogels were formed in Lab/Tek Chamber slider, a microscope glass equipped with a top divider into several compartments. After incubation the top divider was pulled out and the 3D gel remained intact on the microscope slide. The gels on the slide were then viewed with a confocal microscope ×660 using appropriate excitation and emission wavelengths. It was shown that live and dead cells from within the matrix and represents the ability of the hydrogel to support cell growth within the matrix. It is desirable that cells will penetrate into the gel and will support activity and growth of osteoblasts and by additional factors embedded within the hydrogel will suppress growth and activity of osteoclasts. FIG. 4 shows the results of the cryostat technique in which the hydrogel that was incubated with cells was washed with OCT (Optimal Cuttin Temp). The sample was then frozen and cut into slices using a microtom. Each slice was then fixated and stained with Hematoxylin & Eosin. This staining required dehydration therefore the gel appears in FIG. 4 as fibers.

Example 8

RGD Peptide Addition

Osteoblast adhesion takes place by different mechanisms. The most investigated one implies the interaction with RGD (Arg-Gly-Asp) sequences via cell-membrane integrin receptors. In this experiment, the adherence of $SaOS_2$ cells onto hydrogel based on RGD-containing peptide and hydrogel based on peptides having no RGD sequence is compared.

Two hydrogels were prepared: $P_{FD}$-13 (Pro-(Phe-Asp)$_3$)-Pro, SEQ ID NO:34) and $P_{FD}$-13 containing 1% of $P_{FE}$-

Figure 3A:
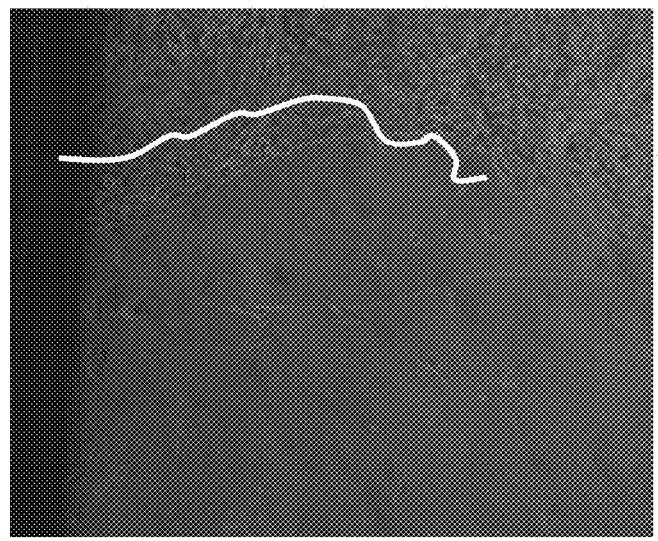
FIG. 3 presents inverted-microscope images of SaOS$_2$ cells on a 2D hydrogel system after 10 days of incubation. A) cells on top of the FD hydrogel. B) cells on top of the FD-RGD hydrogel. The hydrogel-glass border is marked with white line.
Figure 3B:
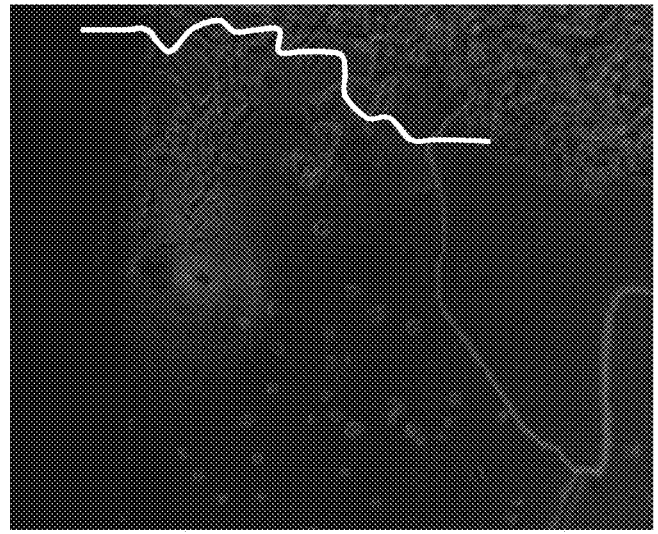

RGDS ((Phe-Glu)-3-Pro-(Gly)-3-Arg-Gly-Asp-Ser, SEQ ID NO:18), and a very thin layer of each hydrogel was spread onto a cover-slip. Aggregated cell suspension of SaOS$_2$ cells was seeded onto the same cover-slip beside the hydrogel. Cell-media was added to cover both, the hydrogel and the cells. As seen in FIG. 3, the combination of P$_{FD}$-13 and FE-RGD hydrogel provides a better environment for cell adhesion and spreading.

Example 9

Additional In-Vitro Experiments

The presence of calcium and phosphate ions may accelerate the biological formation of hydroxyapatite, in addition the composite-hydrogel may improve the mechanical strength of the gel.

In order to improve the rheological properties of the hydrogel the effect of polysaccharide on the peptide hydrogel properties is evaluated in context of cell viability.

Specific histological staining procedures to opaque or transparent 3D matrices are tested for monitoring cell viability, proliferation and biomineralization.

Example 10

Additional Peptides

Additional peptides were studies in order to elucidate the role of termini Proline residue in hydrogel formation, to test the effect of peptide length and peptide termini protecting groups. The following table summarizes the results in terms of formation of hydrogels under specific conditions, i.e. weight concentration (4% in 100 μl NaOH solution) in which peptide P$_{FD}$-13 does form hydrogel.

TABLE 4

Formation of hydrogels by additional peptides.

| Peptide | NaOH conc. | Self supporting gel formation assigned + | Resultant pH |
|---|---|---|---|
| (Phe-Asp)$_6$ | 0.03 | + | ~6 |
| (Phe-Asp)$_6$ | 0.05 | + | ~7 |
| Pro-Asp-(Phe-Asp)$_6$ | 0.03 | + | ~6 |
| Pro-Asp-(Phe-Asp)$_6$ | 0.05 | + after several hrs. | ~7 |
| Ac-Pro-Asp-(Phe-Asp)$_5$-Pro-NH$_2$ | 0.03 | + | ~6 |
| Ac-Pro-Asp-(Phe-Asp)$_5$-Pro-NH$_2$ | 0.05 | Viscous liquid | >7.5 |
| Pro-Asp-Phe-Asp | 0.03 | liquid | ~3 |
| Pro-Asp-Phe-Asp | 0.05 | liquid | ~4 |

Example 11

In-Vivo Experiments

Toxicity, immunity and efficacy tests were and are performed demonstrating the safety and activity of the compositions of the present invention for prevention of progression and treatment of osteoporetic related conditions. The effect on bone augmentation and regeneration is studied on small to medium animals in holes (defects) created in osteoporetic induced bones.

Example 11A

Regeneration of Vertebra in Osteoporetic Rat

This in vivo model is based on the work of Wang, et al. (The Spine Journal 2008, 8, 340-350) on bioreactivity and osteoconductivity of calcium sulfate-based bone cements in response to osteoporotic conditions.

At age 8 weeks, female Sprague Dawley rats are ovarectomized and maintained on a low calcium diet (0.01% calcium, 0.77% phosphate) for 3 months as described by Saito et al. (2002). Before surgery, animals are anesthesized.

Under sterile conditions, a posterior midline incision is made along the proximal tail exposing the dorsal aspect of caudal vertebral bodies. A needle is inserted into the trabecular bone of the vertebral body.

For each animal, two vertebral defects are filled with 0.1 cc of amphiphilic and acidic peptide hydrogels or viscous solution. A randomized unfilled vertebral defect is left as a surgical internal control. The dorsal muscles and tendons are repositioned and closed with monofilament suture.
Evaluation of Bone Regeneration After peptide solution injection, micro-CT imaging is performed on the caudal spine of each group on the day of surgery and, subsequently, at weeks 2, 4, 6, and 8. Bone mineral density (BMD) is determined in addition to average cortical thickness (ACT), bone volume fraction (BVF), average trabecular thickness (TbTh), and trabecular spacing (TbSp). ACT is determined at the diaphysis of the caudal vertebral body. To evaluate the diaphyseal cortical bone concentration, BVF is measured using a 1-mm$^3$ region of interest located 0.5 mm from the ventral aspect of the diaphyseal cortex. Analysis of the trabecular network (TbTh and TbSp) consist of a 1-mm$^3$ region of interest, used to sample trabecular bone 1 mm from the center of the vertebral end plate.

Example 11B

Enhancement of Osteoporotic Vertebral Bodies in an Ovine Model

Prevention of osteoporotic vertebral fractures could help at-risk individuals avoid the pain and morbidity associated with these fractures. Currently, patients with osteoporosis are treated with systemic medications to reduce fracture risk. Although effective, these therapies do not eliminate fractures and also tend to have a gradual time-dependent effect on fracture risk. The compositions of the present invention are candidates for enhancing local bone mineral density.

This in vivo model analyzes the effect of compositions according to the present invention on osteoporotic ovine vertebral architecture and biomechanics. The model is based on the work of Phillips et al., 2006 (The Spine Journal 6, 500-506), which tested the effect of bone morphogenetic protein (BMP-7, known also as osteopgenic protein 1).

Briefly, skeletally mature sheep undergo ovariectomy and are placed on low cation relative to anion diet. These interventions reduce bone density and induce skeletal fragility. After six months, sheep are randomly assigned to different treatment groups of different hydrogel compositions and controls with four animals/treatment group. After creating an 8-mm-diameter defect in the midvertebral body, sheep undergo intravertebral body implantation at two nonadjacent levels. Animals are euthanized six months after implantation and bone mineral density (BMD), biomechanics, and histomorphometry are assessed.

Example 11C

Osteoporosis Model in Rats

The in vivo test is based on the test described in Blouin et al. 2006. In this model, the effects of hormonal deprivation (due to ORx) with disuse (due to BTX paralysis) are cumulative and induce a massive bone loss. Briefly, mature male Wistar rats 5-6 months old, and weighting 600+−75 g are acclimated for 2 weeks (24° C. and a 12-h/12-h light/dark cycle). The control group is anaesthetized (with Isoflurane), nonoperate and receive 0.2 mL of physiological saline in the quadriceps femoris of the right hind limb. To induce a massive bone loss rats will be orchidectomized (ORx) and receive a single injection of *Clostridium botulinum* neurotoxin (BTX) in the quadriceps femoris of the right hind limb. Rats are anaesthetized, orchidectomized bilaterally after scrotal incision and ligature of testicular arteries. Rats are injected intramuscularly BTX. Each animal receive 2U of BTX dissolved in 0.4 mL (2×0.2 mL) physiological saline in the quadriceps femoris of the right hindlimb. These rats constitute the osteoporotic (OP) group that is used for bone defect studies. To evaluate the effect of compositions comprising acidic and amphiphilic b-sheet peptide (AAβP) hydrogels rats are ORX-BTX operated. At certain periods (for example ½, 1 and 2 months) after the ORX-BTX operation, the external side of the right hindlimb is incised. A hole is drilled in the femur cortex with a low rotational speed dentist motor. The composition comprising the AAβP is injected with a canulla and soft tissue is closed after disinfection. X-ray examination is done under isoflurane anaesthesia, 3 days after injection, to ensure that the biomaterial was injected correctly. Rats are weighed weekly and sacrificed by asphyxiation with $CO_2$. One month and two months after the administration of the tested compositing, dissection of the right and left femurs is fixed at 4° C. and during 24 h (in a solution made of 37% formaldehyde: 100 mL, 95° ethanol: 750 mL, $H_2O$: 150 mL). After fixation bone samples are stored in acetone. X-ray microtomography MicroCT is performed on the distal femur. Samples introduced in an Eppendorf tube filled with water. Femurs are embedded undecalcified in methylmethacrylate at 4° C. to maintain enzyme activity. Sections (7-μm thick) are cut dry on a heavy-duty microtome equipped with 50° tungsten carbide knives. Quantitative measurements are performed on a semiautomatic image analyzer system. For each rat, four sections are stained with a modified Goldner trichrome and used for the measurement of osteoid parameters. Four additional sections are used for the identification of the tartrate-resistant acid phosphatase (TRAcP) and counterstained with phosphomolybdic aniline blue to determine the number of osteoclasts. Mineral apposition rate are measured at a magnification of 400× in the cortical and trabecular bone on four unstained sections.

Example 11D

In Vivo Toxicity

The toxicity tests determine the safety of a single subcutaneous administration of hydrogel comprising the peptide Ac-Pro-Asp-(Phe-Asp)-5-Pro-NH$_2$ (SEQ ID NO:19), in Sprague-Dawley rats in an amount that is about 10 times that expected to be clinically relevant in bone treatment (relative to body mass). A control group was injected with saline. Rats were sacrificed after 14 days. Hematology and biochemistry blood tests were performed, the injected area was excised and examined as well as other internal organs.

All rats survived the tests and there were no signs of abnormal behavior. Rats did not lose weight compare to control group and the internal organs appeared normal. Rats that were scarified after 7 days showed slightly high levels of LDH. These were normal for the rats that were scarified after 14 days. The injected gels could not been seen with naked eye at the sight of injection after 7 days and after 14 days.

Example 11E

Antigenicity Tests

Immunity tests were performed to determine the safety of the compositions of the present invention. In one experiment, a single intramuscular administration of hydrogel comprising the peptide Ac-Pro-Asp-(Phe-Asp)-5-Pro-NH$_2$ (SEQ ID NO:19), at 7.5 times the maximum does estimated to be used for treatment in human, to Sprague-Dawley rats was tested. rats. The control group was injected with saline. Rats were scarified after 14 days, blood was withdrawn for future hematology and biochemistry tests. All rats survived the experiment and appeared normal during the experiment.

Example 11F

Biodegradation test

In developing a composition for injection into the bone the in vivo degradation rate of the composition is very important since there is need that the injected material will allow bone cells to growth and develop in the void location. If the injected composition is not degradable, it will occupy the place of the growing bone and will not allow its development. Biodegradation of the hydrogels is tested subcutaneously and intramuscularly. Sprague-Dawley rats received a single subcutaneous administration of hydrogel comprising the peptide Ac-Pro-Asp-(Phe-Asp)$_5$-Pro-NH$_2$, in an amount that is about 10 times that expected to be clinically relevant in bone treatment (relative to body mass). A control group was injected with saline. Seven days after the injection the animals were sacrificed and the hydrogel could have no longer been observed by naked eye. The hydrogel could have physically disintegrated as it was located in a site of the body that is flexible and susceptible to external forces. In general the hydrogel physical and biological degradations can be controlled by the various other peptides mentioned in this invention, the addition of mineral and other polymers, such as polysaccharides.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

LIST OF REFERENCES

Addadi, L.; Weiner, S., Proceedings of the National Academy of Sciences of the United States of America 1985, 82, 4110-4114.
Birdi K. S., Self-assembly monolayer structures of lipids and macromolecules at interfaces. New York: Kluwer Academic/Plenum Publishers, 1999.
Blouin et al., Journal of Biomedical Materials Research, 2006, 78A, 570.
Bolander M E. Proc Soc Exp Biol Med. 200(2):165-70. 1992
Boskey, A. L. Journal of Cellular Biochemistry 1998, 83-91.
Caplan et al., Biomacromolecules, 2000, 1, 627 and 2001, 4, 627.
Colombier et al., Cells Tissues Organs 164:131-140, 1999.
DeGrado, W. F.; Lear, J. D. J. American Chemical Society 1985, 107, 7684-7689.
Ganss, B., Kim, R. H. & Sodek, J. Bone sialoprotein. *Crit. Rev. Oral. Biol. Med.* 10, 79-98 (1999).
Gilbert et al, J Biol. Chem., 275(21):16213-8. 2000
Goldberg et al., Connect Tissue Res., 42(1):25-37. 2001.
He et al., Biochemistry, 44(49):16140-8 2005.
Hollinger and Kleinschmidt, J Craniofacial Surg 1:60-68, 1990.
Hollinger et al. (J Orthop Res. 2007).
Holmes et al., Proc. Natl. Acad. Sci. USA 2000, 97, 6728.
Hunter et al., Journal of Dental Research 1996, 75, 913-913.
Hunter Et al., Biochem. J. 317, 59-64 (1996).
Iijima et al., Journal of Crystal Growth 1998, 193, 182-188.
Ilvesaro et al. Experimental cell research, 1998, 242, 75-83.
Jayawama et al., Adv. Mat. 2006, 18, 611-614.
Knut Strømsøe, Injury, Int. J. Care Injured, 2004, 35, 107-113.
Koh C. J. and Atala A., 2004, J Am Soc Nephrol 15:1113-1125.
Kokubo et al., J Biomed Mater Res. 1990. 24(6): 721-34.
LeGeros, R Z. Clin Orthop 395:81-98, 2002.
Lopes and Pereira, 2007, Brazilian Journal of Medical and Biological Research, 40, 435-442.
Lowenstam, H. A. & Weiner, S. On biominerlaization. (Oxford University Press, New York; 1989).
Mann, S., Biomineralization: principles and concepts in bioinorganic material chemistry. ed.; Oxford University Press: New York, 2001; 'Vol.' p.
Mann, S, Nature 1988, 332, 119-124.
Matsuyama et al. J. Spinal Disord. Tech 2004; 17:291-296.
OU-Yang et al., 2000, Biopolymers (Biospectroscopy) 57: 129-139.
Oldberg et al., J. Biol. Chem. 263, 19430-19432 (1988).
Oliveira et al., Current Opinion in Solid State & Materials Science 2003, 7, 309-318.
Rapaport et al., J. Am. Chem. Soc. 122, 12523-12529 (2000).
Rapaport et al., J. Am. Chem. Soc. 124, 9342-9343 (2002).
Saito et al. (Biomaterials 2002, 23, 2711-6)
Silva et al., Science 2004, 303, 1352.
Sydney L., 2006, Bonnick Clinical Cornerstone, Management of Osteoporosis, 8, 28-39.
Teraub et al., PNAS USA 1989, 86, 9822-9826.
Valentin, A H and Weber, J. Keio J. Med. 53(3):166-71. 2004.
Weiner, S., Addadi, L. Journal of Materials Chemistry 1997, 7, 689-702.
Young et al., Structure, expression and regulation of the major noncollagenous matrix proteins of bone. *Clin. Orthop.* 281, 275-294 (1992).
Zhang S., Nat. Biotechnol. 2003, 21, 1171.

---

What is claimed is:

1. A method for treatment of progression of osteoporosis or pre-osteoporotic condition comprising promoting biomineralization to treat such condition in a patient in need thereof, by direct administration involving injection or implantation of a therapeutically effective amount of a biodegradable hydrogel composition comprising a hydrogel formed by at least one amphiphilic peptide, derivative or salt thereof that forms a β-sheet structure that promotes biomineralization, wherein said biodegradable hydrogel composition is capable of attracting and sustaining calcium ions and wherein the at least one amphiphilic peptide consists of an amino acid sequence of:

X-(Phe-Glu)$_n$-B
X-(Phe-Asp)$_n$-B
X-(Leu-Glu)$_n$-B
X-(Leu-Asp)$_n$-B wherein n designates an integer of 2-9, X designates Pro, Pro-hydrophilic or represents the amino terminus of Phe or Leu, and B is Pro or represents the carboxy terminus of Glu or Asp, and wherein hydrophilic designates an amino acid residue selected from the group consisting of: Glu and Asp.

2. The method of claim 1, wherein the at least one amphiphilic peptide comprises at least one terminal Pro residue.

3. The method of claim 1, wherein the at least one amphiphilic peptide comprises at least one modification selected from a modification of the amino terminus X and modification of the carboxy terminus B.

4. The method of claim 1, wherein the at least one amphiphilic peptide comprises at least one modification selected from of acetylation of the amino terminus X and an amidation of the carboxy terminus B.

5. The method of claim 1, wherein the at least one amphiphilic peptide comprises a sequence selected from the group consisting of:

Pro-Glu-(Phe-Glu)$_9$ (SEQ ID NO: 36) wherein 0 to 6 of the 9 (Phe-Glu) repeats can be absent;
Pro-(Glu-Leu)$_9$-Glu-Pro (SEQ ID NO: 41) wherein 0 to 6 of the 9 (Glu-Leu) repeats can be absent;
Pro-(Asp-Phe)$_9$-Asp-Pro (SEQ ID NO: 42) wherein 0 to 6 of the 9 (Asp-Phe) repeats can be absent;
Pro-(Asp-Leu)$_9$-Asp-Pro (SEQ ID NO: 43) wherein 0 to 6 of the 9 (Asp-Leu) repeats can be absent;

Pro-Glu-(Phe-Glu)$_5$; (SEQ ID NO: 1)
Pro-(Glu-Leu)$_5$-Glu-Pro; (SEQ ID NO: 6)
Pro-(Asp-Leu)$_5$-Asp-Pro; (SEQ ID NO: 7)
Ac-Pro-Asp-(Phe-Asp)$_5$-Pro-NH$_2$; (SEQ ID NO: 19);
Pro-Asp-(Phe-Asp)$_6$; (SEQ ID NO: 20)
(Phe-Asp)$_6$; (SEQ ID NO: 21)
Pro-Glu-(Phe-Glu)$_5$-Pro; (SEQ ID NO: 22)
Pro-Asp-(Phe-Asp)$_5$-Pro-NH$_2$; (SEQ ID NO: 23);
(Phe-Glu)$_5$; (SEQ ID NO: 24)
(Phe-Glu)$_6$; (SEQ ID NO: 25)
(Phe-Glu)$_7$; (SEQ ID NO: 26)
Pro-Asp-(Phe-Asp)$_4$; (SEQ ID NO: 27)
Pro-Asp-(Phe-Asp)$_6$; (SEQ ID NO: 28)
Pro-Asp-(Phe-Asp)$_8$; (SEQ ID NO: 29)
(Phe-Asp)$_5$; (SEQ ID NO: 30)
(Phe-Asp)$_6$; (SEQ ID NO: 31)
(Phe-Asp)$_7$; (SEQ ID NO: 32)
and
Pro-(Phe-Asp)$_3$-Pro. (SEQ ID NO: 34)

6. The method of claim 1, wherein the composition comprises pre-loaded mineral-salt solution or aggregates.

7. The method of claim 6, wherein the pre-loaded mineral salt is a calcium phosphate mineral selected from the group consisting of amorphous calcium phosphate, tricalcium phosphate and hydroxyapatite.

8. The method of claim 1, wherein the composition comprises pre-loaded polysaccharide.

9. The method of claim 8, wherein the pre-loaded polysaccharide is selected from the group consisting of: hyaluronic acid, alginate and sulfated polysaccharide.

10. The method of claim 9, wherein the composition comprises the sequence Ac-Pro-Asp-(Phe-Asp)$_5$-Pro-NH$_2$ (SEQ ID NO: 19) and further comprises alginate.

11. The method of claim 1, wherein the composition further comprises at least one therapeutic agent.

12. The method of claim 11, wherein the therapeutic agent is selected from the group consisting of: active protein, growth factor, cytokine, chemotherapeutic drug, enzyme, anti-microbial, anti-resorptive agent, hormone, and anti-inflammatory agent.

13. The method of claim 1, wherein the composition is a dry composition or a semi-fluid composition.

14. The method of claim 1, wherein the composition is administered into porous or hollow bone.

15. The method of claim 1, wherein the composition is administered into the hip, into a vertebral bone in the spine, into the interior of a vertebra or into a medullary canal of a long bone or wherein the composition is administered into a bone area selected from the group consisting of compact bone, cancellous bone, epiphyseal line, epipysis, and metaphysic.

16. The method of claim 1, wherein the biodegradable hydrogel composition further comprises at least one anti-resorptive agent, and wherein the peptide comprises the sequence Pro-(Asp-Leu)$_9$-Asp-Pro (SEQ ID NO: 43) wherein 0 to 6 of the 9 (Asp-Leu) repeats can be absent.

17. The method of claim 16, wherein the composition comprises pre-loaded mineral-salt solution, polysaccharides, or aggregates, and is administered into hollow or porous bone in the hip, into a vertebral bone in the spine, into the interior of a vertebra, into a medullary canal of a long bone, or into a bone area selected from the group consisting of compact bone, cancellous bone, epiphyseal line, epipysis, and metaphysic.

18. The method of claim 12 wherein the anti-resorptive agent is a bisphosphonate.

19. The method of claim 18, wherein the bisphosphonate is selected from the group consisting of alendronate, clodronate, etidronate, ibandronate, icadronate, pamidronate, risedronate, tiludronate and zoledronate.

20. The method of claim 1, wherein n designates an integer of 2 to 8.

21. The method of claim 1, wherein n designates an integer of 3 to 7.

22. The method of claim 1, wherein n designates an integer of 3 to 6.

* * * * *

UNITED STATES PATENT AND TRADEMARK OFFICE
CERTIFICATE OF CORRECTION

PATENT NO. : 9,457,056 B2
APPLICATION NO. : 12/746168
DATED : October 4, 2016
INVENTOR(S) : Rapaport Page 1 of 1

It is certified that error appears in the above-identified patent and that said Letters Patent is hereby corrected as shown below:

In the specification

Column 7:
Line 62, delete "(SEQ ID NO: 36)wherein" and insert -- (SEQ ID NO: 36) wherein --.
Line 66, delete "SEQ ID NO: 38)wherein" and insert -- (SEQ ID NO: 38) wherein --.

Column 8:
Line 12, delete "(SerPO$_4$-Leu)" and insert -- (Ser-Leu) --.

In the claims

Column 62:
Line 27, after "(SEQ ID NO: 19)", delete ";".
Line 37, after "(SEQ ID NO: 23)", delete ";".

Signed and Sealed this
Eighth Day of November, 2016

Michelle K. Lee
*Director of the United States Patent and Trademark Office*

SEQUENCE LISTING

```
<160> NUMBER OF SEQ ID NOS: 47

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 1

Pro Glu Phe Glu Phe Glu Phe Glu Phe Glu Phe Glu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

Glu Phe Glu Phe Glu Phe Glu Phe Glu Phe Glu Pro
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide
```

```
-continued

<400> SEQUENCE: 3

Pro Ser Phe Ser Phe Ser Phe Ser Phe Ser Phe Ser Pro
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 4

Pro Ser Phe Ser Phe Ser Phe Ser Phe Ser Phe Ser Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 5

Pro Tyr Phe Tyr Phe Tyr Phe Tyr Phe Tyr Phe Tyr Pro
1               5                   10
```

-continued

```
<210> SEQ ID NO 6
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 6

Pro Glu Leu Glu Leu Glu Leu Glu Leu Glu Leu Glu Pro
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 7

Pro Asp Leu Asp Leu Asp Leu Asp Leu Asp Leu Asp Pro
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 8

Pro Ser Leu Ser Leu Ser Leu Ser Leu Ser Leu Ser Pro
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 9

Pro Ser Leu Ser Leu Ser Leu Ser Leu Ser Leu Ser Pro
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 10

Pro Tyr Leu Tyr Leu Tyr Leu Tyr Leu Tyr Leu Tyr Pro
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 11

Pro Glu Phe Ser Phe Glu Phe Ser Phe Glu Phe Ser Phe Glu Phe Ser
1               5                   10                  15

Phe Glu Pro

<210> SEQ ID NO 12
<211> LENGTH: 19
<212> TYPE: PRT
<213> ORGANISM: Artificial Sequence
<220> FEATURE:
<223> OTHER INFORMATION: Synthetic Peptide in which 0 to 3 of the 4
      (Ser-Phe-Ser-Phe) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
```

<400> SEQUENCE: 12

Pro Ser Phe Ser Phe Ser Phe Ser Phe Ser Phe Ser Phe Ser Phe Ser
1               5                   10                  15

Phe Ser Pro

<210> SEQ ID NO 13
<211> LENGTH: 21
<212> TYPE: PRT
<213> ORGANISM: Artificial Sequence
<220> FEATURE:
<223> OTHER INFORMATION: Synthetic Peptide in which 0 to 3 of the 4
      (Ser-Phe-Glu-Phe) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 13

Pro Ser Phe Glu Phe Ser Phe Glu Phe Ser Phe Glu Phe Ser Phe Glu
1               5                   10                  15

Phe Glu Pro Ser Pro
            20

<210> SEQ ID NO 14
<211> LENGTH: 19
<212> TYPE: PRT
<213> ORGANISM: Artificial Sequence
<220> FEATURE:
<223> OTHER INFORMATION: Synthetic Peptide in which 0 to 3 of the 4
      (SerPO4-Phe-Asp-Phe) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 14

Pro Ser Phe Asp Phe Ser Phe Asp Phe Ser Phe Asp Phe Ser Phe Asp
1               5                   10                  15

Phe Asp Pro

<210> SEQ ID NO 15
<211> LENGTH: 30
<212> TYPE: PRT
<213> ORGANISM: Artificial Sequence
<220> FEATURE:
<223> OTHER INFORMATION: Synthetic Peptide

```
<400> SEQUENCE: 15

Ala Leu Glu Phe Glu Phe Glu Phe Glu Pro Ala Glu Phe Glu Phe Glu
1               5                   10                  15

Phe Glu Leu Pro Ala Leu Glu Phe Glu Phe Glu Phe Glu Pro
                20                  25                  30

<210> SEQ ID NO 16
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 16

Pro Glu Phe Glu Phe Glu Lys Glu Phe Glu Phe Glu Pro
1               5                   10

<210> SEQ ID NO 17
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 17

Pro Glu Phe Glu Phe Glu Phe Glu Phe Glu Phe Glu Gly Gly Gly Arg
1               5                   10                  15

Gly Asp Ser

<210> SEQ ID NO 18
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 18

Phe Glu Phe Glu Phe Glu Pro Gly Gly Gly Arg Gly Asp Ser
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: AMIDATION

<400> SEQUENCE: 19

Pro Asp Phe Asp Phe Asp Phe Asp Phe Asp Phe Asp Pro
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 20

Pro Asp Phe Asp Phe Asp Phe Asp Phe Asp Phe Asp Phe Asp
1               5                   10
```

```
<210> SEQ ID NO 21
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 21

Phe Asp Phe Asp Phe Asp Phe Asp Phe Asp Phe Asp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 22

Pro Glu Phe Glu Phe Glu Phe Glu Phe Glu Phe Glu Pro
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: AMIDATION

<400> SEQUENCE: 23

Pro Asp Phe Asp Phe Asp Phe Asp Phe Asp Phe Asp Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 24

Phe Glu Phe Glu Phe Glu Phe Glu Phe Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 25

Phe Glu Phe Glu Phe Glu Phe Glu Phe Glu Phe Glu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic Peptide
```

```
<400> SEQUENCE: 26

Phe Glu Phe Glu Phe Glu Phe Glu Phe Glu Phe Glu Phe Glu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Pro Asp Phe Asp Phe Asp Phe Asp Phe Asp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 28

Pro Asp Phe Asp Phe Asp Phe Asp Phe Asp Phe Asp Phe Asp
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 29

Pro Asp Phe Asp Phe Asp Phe Asp Phe Asp Phe Asp Phe Asp Phe Asp
1               5                   10                  15

Phe Asp

<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

Phe Asp Phe Asp Phe Asp Phe Asp Phe Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 31

Phe Asp Phe Asp Phe Asp Phe Asp Phe Asp Phe Asp
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Peptide
```

```
<400> SEQUENCE: 32

Phe Asp Phe Asp Phe Asp Phe Asp Phe Asp Phe Asp Phe Asp
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 33

Pro Asp Phe Asp Phe Asp Phe Asp Phe Asp Phe Asp Pro Arg Gly Asp
1               5                   10                  15

Ser

<210> SEQ ID NO 34
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 34

Pro Phe Asp Phe Asp Phe Asp Pro
1               5

<210> SEQ ID NO 35
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 35

Pro Phe Asp Phe Asp Phe Asp Pro Gly Gly Gly Arg Gly Asp Ser
1               5                   10                  15

<210> SEQ ID NO 36
<211> LENGTH: 20
<212> TYPE: PRT
<213> ORGANISM: Artificial Sequence
<220> FEATURE:
<223> OTHER INFORMATION: Synthetic Peptide in which 0 to 6 of the 9
      (Phe-Glu) repeats can be absent

<400> SEQUENCE: 36

Pro Glu Phe Glu Phe Glu Phe Glu Phe Glu Phe Glu Phe Glu Phe Glu
1               5                   10                  15

Phe Glu Phe Glu
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic Peptide in which 0 to 6 of the 9
      (Phe-Glu) repeats can be absent

<400> SEQUENCE: 37

Glu Phe Glu Phe Glu Phe Glu Phe Glu Phe Glu Phe Glu Phe Glu Phe
1               5                   10                  15

Glu Phe Glu Pro
            20
```

```
<210> SEQ ID NO 38
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Ser-Phe) repeats can be absent

<400> SEQUENCE: 38

Pro Ser Phe Ser Phe Ser Phe Ser Phe Ser Phe Ser Phe Ser Phe Ser
1               5                   10                  15

Phe Ser Phe Ser Pro
            20

<210> SEQ ID NO 39
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Ser-Phe) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION

<400> SEQUENCE: 39

Pro Ser Phe Ser Phe Ser Phe Ser Phe Ser Phe Ser Phe Ser Phe Ser
1               5                   10                  15

Phe Ser Phe Ser Pro
            20

<210> SEQ ID NO 40
<211> LENGTH: 21
<212> TYPE: PRT
<213> ORGANISM: Artificial Sequence
```

```
<220> FEATURE:
<223> OTHER INFORMATION: Synthetic Peptide in which 0 to 6 of the 9
      (Tyr-Phe) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION

<400> SEQUENCE: 40

Pro Tyr Phe Tyr Phe Tyr Phe Tyr Phe Tyr Phe Tyr Phe Tyr Phe Tyr
1               5                   10                  15

Phe Tyr Phe Tyr Pro
            20

<210> SEQ ID NO 41
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Glu-Leu) repeats can be absent

<400> SEQUENCE: 41

Pro Glu Leu Glu Leu Glu Leu Glu Leu Glu Leu Glu Leu Glu Leu Glu
1               5                   10                  15

Leu Glu Leu Glu Pro
            20

<210> SEQ ID NO 42
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Asp-Phe) repeats can be absent
```

```
<400> SEQUENCE: 42

Pro Asp Phe Asp Phe Asp Phe Asp Phe Asp Phe Asp Phe Asp
1               5                   10                  15

Phe Asp Phe Asp Pro
            20

<210> SEQ ID NO 43
<211> LENGTH: 21
<212> TYPE: PRT
<213> ORGANISM: Artificial Sequence
<220> FEATURE:
<223> OTHER INFORMATION: Synthetic Peptide with variable lengths in
      which 0 to 6 of the 9 (Asp-Leu) repeats can be absent

<400> SEQUENCE: 43

Pro Asp Leu Asp Leu Asp Leu Asp Leu Asp Leu Asp Leu Asp Leu Asp
1               5                   10                  15

Leu Asp Leu Asp Pro
            20

<210> SEQ ID NO 44
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Ser-Leu) repeats can be absent

<400> SEQUENCE: 44

Pro Ser Leu Ser Leu Ser Leu Ser Leu Ser Leu Ser Leu Ser Leu Ser
1               5                   10                  15

Leu Ser Leu Ser Pro
            20

<210> SEQ ID NO 45
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Ser-Leu) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
```

```
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION

<400> SEQUENCE: 45

Pro Ser Leu Ser Leu Ser Leu Ser Leu Ser Leu Ser Leu Ser Leu Ser
1               5                   10                  15

Leu Ser Leu Ser Pro
            20

<210> SEQ ID NO 46
<211> LENGTH: 21
<212> TYPE: PRT
<213> ORGANISM: Artificial Sequence
<220> FEATURE:
<223> OTHER INFORMATION: Synthetic Peptide in which 0 to 6 of the 9
      (Tyr-Leu) repeats can be absent
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION

<400> SEQUENCE: 46

Pro Tyr Leu Tyr Leu Tyr Leu Tyr Leu Tyr Leu Tyr Leu Tyr Leu Tyr
1               5                   10                  15

Leu Tyr Leu Tyr Pro
            20
```

```
<210> SEQ ID NO 47
<211> LENGTH: 39
<212> TYPE: PRT
<213> ORGANISM: Artificial Sequence
<220> FEATURE:
<223> OTHER INFORMATION: Synthetic Peptide in which 0 to 6 of the 9
      (Glu-Phe-Ser-Phe) repeats can be absent

<400> SEQUENCE: 47

Pro Glu Phe Ser Phe Glu Phe Ser Phe Glu Phe Ser Phe Glu Phe Ser
1               5                   10                  15

Phe Glu Phe Ser Phe Glu Phe Ser Phe Glu Phe Ser Phe Glu Phe Ser
                20                  25                  30

Phe Glu Phe Ser Phe Glu Pro
                35
```